United States Patent [19]
Elias et al.

[11] Patent Number: 6,060,515
[45] Date of Patent: May 9, 2000

[54] TREATMENT OF SKIN CONDITIONS BY USE OF PPARα ACTIVATORS

[75] Inventors: Peter M. Elias, Mill Valley; Nathan N. Bass, San Francisco; Karen Hanley, Mill Valley; Kenneth R. Feingold, San Rafael, all of Calif.

[73] Assignee: The Regents of the University of California, Oakland, Calif.

[21] Appl. No.: 09/101,366

[22] Filed: Jun. 16, 1999

Related U.S. Application Data

[63] Continuation-in-part of application No. PCT/US98/01276, Jan. 22, 1998, which is a continuation of application No. 08/788,973, Jan. 24, 1997, abandoned.

[51] Int. Cl.⁷ .................................................. A61K 31/20
[52] U.S. Cl. ........................... 514/560; 514/256; 514/543
[58] Field of Search ..................................... 514/256, 543, 514/560

[56] References Cited

FOREIGN PATENT DOCUMENTS 0 447 318 B1   5/1995   European Pat. Off. .

WO 94/21230   9/1994   WIPO .

OTHER PUBLICATIONS

CA 126:142392, Arts et al., 1997.
Forman et al. *Cell* (Jun. 2, 1995) 81: 687–693.
Hanley et al. *The Journal of Investigative Dermatology* (Mar. 1996) 106(3): 404–411.
Imakado et al. *Genes Dev.* (1995) 9(3): 317–329.
Schmidt et al. *Lipids* (1996) 31(11): 1115–1124.
Schoonjans et al. *Journal of Lipid Research* (1996) 37: 907–925.
Weinberger *TEM* (1996) 7(1): 1–6.
Yang et al. *Br. J. Dermatol.* (1995) 133(5): 679–685.

*Primary Examiner*—Rebecca Cook
*Attorney, Agent, or Firm*—Townsend and Townsend and Crew LLP

[57] ABSTRACT

Disorders of the skin and mucous membrane that have a disrupted or dysfunctional epidermal barrier are treated or prevented by topical application of compounds that are either activators of the farnesoid X receptor, activators of the peroxisome proliferator-activated receptor α, and oxysterol activators of the LXRα receptor. The same compounds are also effective in treating disorders of epidermal differentiation and proliferation.

18 Claims, 29 Drawing Sheets

TREATMENT OF SKIN CONDITIONS BY USE OF PPARα ACTIVATORS

CROSS REFERENCE TO RELATED APPLICATION

This is a continuation in part of PCT/US 98/01276 filed Jan. 22, 1998 which is a continuation of U.S application Ser. No. 08/788,973, filed Jan. 24, 1997 abandoned and incorporated herein by reference.

GOVERNMENT RIGHTS

This invention was made at least in part with assistance from the United States Federal Government, under Grant No. HD 29706 of the National Institutes of Health. As a result, the Government has certain rights in this invention.

This invention resides in the technical field of topical formulations for application to skin, and to the treatment of subjects suffering from skin or mucous membrane diseases or disorders which display disruptions of the barrier function, and those that involve disorders of epidermal differentiation and proliferation.

BACKGROUND OF THE INVENTION

One of the functions served by the epidermis in mammals is to form a barrier against excessive transcutaneous water loss to the environment. This barrier is formed by the anucleate, cornified, outermost layers of the epidermis, collectively known as the stratum corneum. Localized or generalized perturbations of the epidermal barrier occur in a variety of diseases and conditions of the skin and mucous membrane. These perturbations not only contribute significantly to the morphology of cutaneous lesions, but also activate certain skin diseases such as the Koebner phenomenon in psoriasis and the inflammation in eczematous disorders. The integrity of the barrier is also known to be a major factor in regulating epidermal DNA synthesis. Thus, maintenance of a normal epidermal barrier is a physiological means of inhibiting epidermal hyperproliferation. Examples of conditions that involve or give rise to a disrupted or dysfunctional epidermal barrier are:

- fluid and electrolyte abnormalities, hypothermia, and infection through the skin in premature infants less than 33 weeks of gestational age;
- inflammation to mucous membranes, such as cheilitis, chapped lips, nasal irritation and vulvovaginitis;
- eczematous dermatitides, such as atopic and seborrheic dermatitis, allergic or irritant contact dermatitis, eczema craquelée, photoallergic dermatitis, phototoxic dermatitis, phytophotodermatitis, radiation dermatitis, and stasis dermatitis;
- ulcers and erosions resulting from trauma, burns, bullous disorders, or ischemia of the skin or mucous membranes;
- several forms of ichthyoses;
- epidermolysis bullosae;
- psoriasis;
- hypertrophic scars and keloids;
- cutaneous changes of intrinsic aging and photoaging;
- frictional blistering caused by mechanical shearing of the skin; and
- cutaneous atrophy resulting from the topical use of corticosteroids.

The key constituents of the epidermis that are needed for a functional barrier are the intercellular, lamellar bilayer sheets of stratum corneum lipids. The synthesis of stratum corneum lipids is relatively autonomous from circulating or dietary influences. The synthetic response is regulated instead by alterations in permeability barrier functions. The regulation occurs through changes in the activities, phosphorylation (activation) state, mass, and mRNA for the rate-limiting enzymes of each of the three key lipids: serine palmitoyl transferase (for ceramides), HMGCoA reductase (for cholesterol), and both acetyl CoA carboxylase and fatty acid synthase (for fatty acids). Other results of alterations in barrier function are the regulation of key enzymes of extracellular lipid processing. One such enzyme is β-glucocerebrosidase, which catalyzes the conversion of precursor glycosylceramides into ceramides.

While permeability barrier requirements regulate lipid synthesis, the endogenous regulators of barrier development and homeostasis are not known. Recent studies from the inventors' laboratories have shown that several activators and ligands of the nuclear receptor superfamily, such as glucocorticoids, thyroid hormone, and estrogen, accelerate the appearance of a mature barrier in fetal rodent skin. Hanley, K., et al., "Epidermal barrier ontogenesis: maturation in serum-free media and acceleration by glucocorticoids and thyroid hormone but not selected growth factors," *J. Invest. Dermatol.* 106:404–411 (1996); Hanley, K., et al., "Hormonal basis for the gender difference in epidermal barrier formation in the fetal rat. Acceleration by estrogen and delay by androgen," *J. Invest. Denmatol.* 97:2576–2584 (1996). In contrast, other members of this family, such as 1,25-dihydroxy vitamin $D_3$ 9-cis-retinoic acid, and all-trans-retinoic acid, had no effect.

SUMMARY OF THE INVENTION

It has now been discovered that the formation of a mature, fully differentiated stratum corneum and a functional epidermal permeability barrier are accelerated by the topical administration of certain activators of any one of three nuclear receptors—the farnesoid X-activated receptor (FXR), the peroxisome proliferator-activated receptor α (PPARα), and the liver-based receptor known as LXRα. These three receptors are nuclear receptors and are part of the nuclear receptor superfamily of transcription factors. The three receptors reside in a subgroup of the superfamily, all receptors in the subgroup sharing the feature that they function only when having formed heterodimers with the retinoid X receptor (RXR). Many other members of the subgroup however do not have activators that accelerate the formation of a mature stratum corneum or barrier development—these include the vitamin D receptor (VDR), the all-trans-retinoic acid receptors (RARα,β,δ), and the 9-cis-retinoic acid (RXR) receptor. The ability of FXR, PPARα and LXRα activators to achieve this result is therefore unique among members of this subgroup.

The ability of FXR activators to accelerate barrier development is particularly surprising since compounds similar in structure to farnesol (a prominent FXR activator) that are not themselves FXR activators do not accelerate barrier development, despite the similarity in structure to those that do. Also surprising is the ability of the PPARα receptor, since other PPAR receptors exist (with their own separate activators) that are similar in structure and function, and yet only activators of the PPARα receptor accelerate barrier development. A further surprising aspect of this discovery is that the barrier development acceleration associated with PPARα activation is not related to any distinction between essential and non-essential fatty acids, but rather to certain common structural features. A still further surprising aspect of the discovery relates to oxysterols that are not activators of LXRα but are very close in structure to those that are. The oxysterols that are not LXRα activators do not produce the beneficial results of this invention despite their similarity in structure. Furthermore, many of the activators that are the subject of this invention have never before been known to have any utility as topical epidermal agents.

This newly discovered activity of the three classes of activators renders them useful in the treatment of mammalian skin suffering deficient or perturbed barrier function. The invention is particularly useful in the treatment of premature infants, particularly those less than 33 weeks of gestational age. This invention is also useful for alterations in epidermal differentiation and proliferation. Applications include melanoma and non-melanoma skin cancers and skin precancers, disorders of epidermal differentiation and proliferation such as psoriasis, atopic dermatitis, and various types of ichthyosis with or without an associated barrier abnormality; and benign neoplasms such as warts, condylomata, and seborrheic keratoses.

Other features and advantages of the invention will become apparent from the description that follows.

DETAILED DESCRIPTION OF THE INVENTION AND PREFERRED EMBODIMENTS

Figure 1:
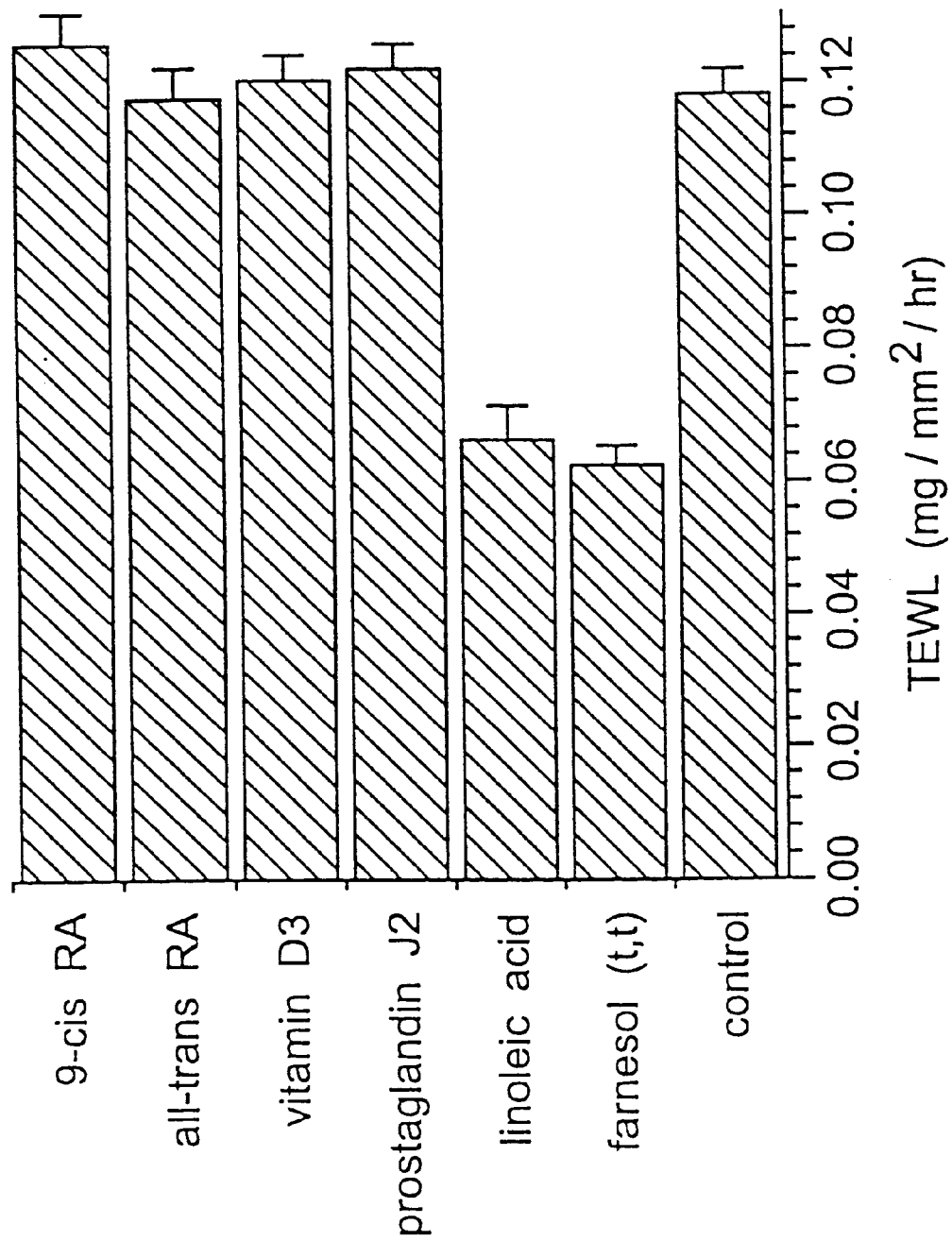
FIG. 1 is a bar graph showing trans-epidermal water loss (TEWL) test results of six compounds, two of which are within the scope of this invention.

The farnesoid X-activated receptor (FXR), the peroxisome proliferator-activated receptor α (PPARα), and the receptor LXRα are members of a superfamily of approximately 150 proteins that bind to cis-acting elements in the promoters of their target genes and modulate gene expression in response to hormone activators or ligands. For many of these receptors, the activators are known, while for others, termed "orphan receptors," the activators are unknown. Furthermore, some of these receptors bind to their target genes as dimers consisting of two molecules of the same receptor (homodimers), while others bind as dimers consisting of one molecule each of two different receptors (heterodimers). Prominent among the latter are nuclear receptors that require heterodimerization with the retinoid X receptor, as disclosed by Yu, V. C., et al., "RXRβ: a coregulator that enhances binding of retinoic acid, thyroid hormone, and vitamin D receptors to their cognate response elements," *Cell* 67:1251–1266 (1991). Members of this group include the vitamin D receptor, the thyroid hormone receptor ($T_3R$), the retinoic acid receptor (RAR), the farnesoid X-activated receptor (FXR), the peroxisome proliferator-activated receptors (PPAR), and LXRα.

The farnesoid X-activated receptor (FXR) was first reported by Forman and coworkers, Forman, B. B., "Identification of a nuclear receptor that is activated by farnesol metabolites," *Cell* 81:687–693 (1995). This receptor is a protein having a relative molecular mass ($M_r$) of approximately 54,000, and is a vertebrate transcription factor regulated by intracellular metabolites. The receptor is activated by certain farnesoids, i.e., farnesol itself and compounds derived from, and/or similar in structure to, farnesol. These farnesoids include farnesol, farnesal, farnesyl acetate, farnesoic acid, geranylgeraniol, and juvenile hormone III. The chemical name for farnesol is 3,7,11,trimethyl-2,6,10-dodecatrienol, and the chemical name for juvenile hormone III is 7-methyl-9-(3,3-dimethyloxiranyl)-3-methyl-2,6-nonadienoic acid methyl ester. Farnesoids and metabolites that do not activate the FXR are geraniol, squalene, methoprene, mevalonate, squalene oxide, squalene dioxide, lanosterol, 24,25-epoxycholesterol, pregnenalone, dehydroepiandrosterone, bile acids, and 25-hydroxycholesterol. FXR activators of particular interest are farnesol (denoting trans,trans-farnesol hereinafter), farnesal, methyl farnesyl ether, ethyl farnesyl ether, methyl farnesoate, ethyl farnesoate, 7-methyl-9-(3,3-dimethyloxiranyl)-3-methyl-2,6-nonadienoic acid methyl ester, and 7-methyl-9-(3,3-dimethyloxiranyl)-3-methyl-2,6-nonadienoic acid ethyl ester. Preferred among these are farnesol, farnesal, methyl farnesyl ether, methyl farnesoate, and 7-methyl-9-(3,3-dimethyloxiranyl)-3-methyl-2,6-nonadienoic acid methyl ester. Particularly preferred are farnesol and 7-methyl-9-(3,3-dimethyloxiranyl)-3-methyl-2,6-nonadienoic acid methyl ester juvenile hormone III).

Peroxisome proliferator-activated receptors (PPAR) are described in a review article by Schoonjans, K., "Role of the peroxisome proliferator-activated receptor (PPAR) in mediating the effects of fibrates and fatty acids on gene expression," *J. Lipid Res.* 37:907–925 (1996). Three subtypes of PPAR have been identified, and these are designated as α, β (or δ), and γ. The α subtype has been cloned from Xenopus, humans, mouse and rat; the β (or δ) subtype from Xenopus, humans and mouse; and the γ subtype from Xenopus, humans and hamster. The PPARs have a modular structure consisting of six functional domains. The one domain that serves as the DNA-binding domain contains about 66 amino acids and is stabilized by two zinc atoms, each binding to four invariant cysteine residues. Included among the activators for PPARα are fibrates, and fatty acids other than short-chain ($<C_{10}$) fatty acids, long-chain monounsaturated fatty acids, and dicarboxylic acids, particularly dodecanedioic acid. Also included are lower alkyl, preferably methyl, esters of the fibrates and lower alkyl, preferably methyl, esters of the fatty acids. Fibrates include:

clofibrate: 2-(4-chlorophenoxy)-2-methylpropanoic acid ethyl ester
fenofibrate: 2-(4-(4-chlorobenzoyl)phenoxy)-2-methylpropanoic acid isopropyl ester
ciprofibrate: 2-(4-(2,2-dichlorocyclopropyl)phenoxy) isobutyric acid
gemfibrozil: 2-(2,4-dimethylphenoxypropyl)-2-methylpropanoic acid
bezafibrate: 2-(4-(4-chlorobenzoylaminoethyl)phenoxy)-2-methylpropanoic acid Among the fatty acids, substituted fatty acids are particularly potent activators. PPARα activators of particular interest are linoleic acid, oleic acid, 5,8,11,14-eicosatetraynoic acid, (4-chloro-6-(2,3-xylidino)-2-pyrimidinyl)thioacetic acid, and clofibrate. A list including these and other examples of PPARα activators is as follows:

2,4-dichlorophenoxyacetic acid
2,4,5-trichlorophenoxyacetic acid
2-methyl-4-chlorophenoxyacetic acid
2-phenoxy-2-methylpropanoic acid ethyl ester
2-(4-bromophenoxy)-2-methylpropanoic acid ethyl ester
2-(4-iodophenoxy)-2-methylpropanoic acid ethyl ester
2-(2-chlorophenoxy)-2-methylpropanoic acid ethyl ester
2-(3-chlorophenoxy)-2-methylpropanoic acid ethyl ester
2-(4-chlorophenoxy)-2-methylpropanoic acid ethyl ester
2-(4-(4-chlorophenyl)phenoxy)-2-methylpropanoic acid ethyl ester
2-(4-(4-chlorobenzoyl)phenoxy)-2-methylpropanoic acid isopropyl ester
2-(4-(2,2-dichlorocyclopropyl)phenoxy)-2-methylpropanoic acid
2-(4-(4-chlorobenzoylaminoethyl)phenoxy)-2-methylpropanoic acid
2-(2,3-dimethyl-4-(1,2,3,4-tetrahydronaphth-1-yl)phenoxy) acetic acid
2-(2-methyl-3-ethyl-4-(4-chlorobenzyl)phenoxy)acetic acid
(4-chloro-6-(2,3-xylidino)-2-pyrimidinyl)thioacetic acid
2-((4-chloro-6-(2,3-xylidino)-2-pyrimidinyl)thioacetamido) ethanol
perfluoro-n-decanoic acid
di-(2-ethylhexyl)adipate
di-(2-ethylhexyl)phosphate
di-(2-ethylhexyl)sebacate
bis-(carboxymethylthio)-1,10-decane
ethyl 4-(4-chlorophenoxy)butanoate
2-(2-nitro-5-(2-chloro-4-trifluoromethylphenoxy) benzoyloxy)propanoic acid ethyl ester
2-(4-(4-chlorobenzoyl))phenoxy-2-(2-methylpropionamido)ethylsulfonic acid
tetradecyloxyacetic acid
tetradecyloxypropionic acid
perfluorobutanoic acid
perfluorooctanoic acid
tetradecylthioacetic acid
tetradecylthiopropionic acid
di-(2-ethylhexyl)phthalate
mono-(2-ethylhexyl)phthalate
2-ethylhexanoic acid
2-propylhexanoic acid The receptor LXRα was first described by Willy, P. J., et al., "LXR, a nuclear receptor that defines a distinct retinoid response pathway," *Genes & Development* 9:1033–1045 (Cold Spring Harbor Laboratory Press), and is named LXRα due to its initial isolation from the liver and its liver-rich expression pattern. The activators of LXRα are a subset of oxysterols, including 7α-hydroxycholesterol, 25-hydroxycholesterol, 27-hydroxycholesterol, 4β-hydroxycholesterol, 24-hydroxycholesterol, 20(S)-hydroxycholesterol, 22(R)-hydroxycholesterol, and 20,22-dihydroxycholesterol. Structurally similar compounds that are not activators of LXRα include cholesterol itself and the oxysterols 7,25-dihydroxycholesterol, 17α-hydroxycholesterol, and 22(S)-hydroxycholesterol (enantiomer of 22(R)-hydroxycholesterol). The numbering convention used for substituted cholesterols is as follows:

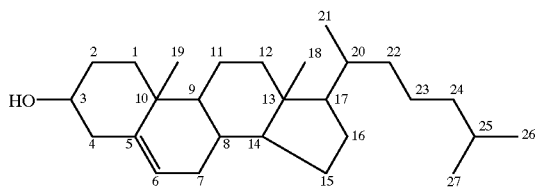

The term "activator" is used in this specification to denote any molecular species that results in activation of the indicated receptor, regardless of whether the species itself binds to the receptor or a metabolite of the species binds to the receptor when the species is administered topically. Thus, the activator can be a ligand of the receptor or it can be an activator that is metabolized to the ligand of the receptor, i.e., a metabolite that is formed in tissue and is the actual ligand.

In the practice of this invention, the activators will be administered as active ingredients in a formulation that is pharmaceutically acceptable for topical administration. These formulations may or may not contain a vehicle, although the use of a vehicle is preferred. Preferred vehicles are non-lipid vehicles, particularly a water-miscible liquid or mixture of liquids. Examples are methanol, ethanol, isopropanol, ethylene glycol, propylene glycol, and butylene glycol, and mixtures of two or more of these compounds.

The concentration of active ingredient in the vehicle will generally range from about 10 $\mu$M to about 1000 $\mu$M, although for certain active ingredients, the concentration may vary outside this range. In formulations containing farnesol as the active ingredient, preferred concentrations are in the range of about 10 $\mu$M to about 100 $\mu$M. In formulations containing juvenile hormone III as the active ingredient, preferred concentrations are in the range of about 10 $\mu$M to about 200 $\mu$M. In formulations containing clofibrate as the active ingredient, preferred concentrations are in the range of about 100 $\mu$M to about 1,000 $\mu$M. In formulations containing oleic acid as the active ingredient, preferred concentrations are in the range of about 100 $\mu$M to about 1000 $\mu$M. In formulations containing linoleic acid as the active ingredient, preferred concentrations are in the range of about 5 $\mu$M to about 50 $\mu$M.

Topical formulations containing the FXR or PPARα activators in accordance with the present invention are applied to beneficial effect to skin and/or mucus membranes. The activators can be formulated as lotions, solutions, gels, creams, emollient creams, unguents, sprays, or any other form that will permit topical application. The formulation may also contain one or more agents that promote the spreading of the formulation over the affected area, but are otherwise biologically inactive. Examples of these agents are surfactants, humectants, wetting agents, emulsifiers, or propellants.

Amounts that are referred to herein as effective in enhancing barrier development are any amount that will cause a substantial relief of the symptoms of a disrupted or dysfunctional epidermal permeability barrier when applied repeatedly over time. The optimum amounts in any given instance will be readily apparent to those skilled in the art or are capable of determination by routine experimentation.

Examples of skin conditions that are susceptible to treatment by the practice of this invention are:

the skin of premature infants of gestational age less than 33 weeks;

atopic and seborrheic dermatitis;

inflammation to mucous membranes, such as cheilitis, chapped lips, nasal irritation and vulvovaginitis;

eczematous dermatitis resulting from allergic and irritant contact, eczema craquelée, radiation and stasis dermatitis;

ulcers and erosions due to chemical or thermal burns, bullous disorders, or vascular compromise or ischemia including venous, arterial, embolic or diabetic ulcers;

ichthyoses, with or without an associated barrier abnormality;

epidermolysis bullosa;

psoriasis;

hypertrophic scars and keloids;

intrinsic aging and/or dermatoheliosus;

mechanical friction blistering;

corticosteroid atrophy; and melanoma and non-melanoma skin cancer, including lignin melanoma, basal cell carcinoma, squamous cell carcinoma, actinic keratoses, and virally induced neoplasia (warts and condylomata accuminata).

Optimal methods and frequency of administration will be readily apparent to those skilled in the art or are capable of determination by routine experimentation. Effective results in most cases are achieved by topical application of a thin layer over the affected area, or the area where one seeks to achieve the desired effect. Depending on the condition being addressed, its stage or degree, and whether application is done for therapeutic or preventive reasons, effective results are achieved with application rates of from one application every two or three days to four or more applications per day.

The invention is generally applicable to the treatment of the skin of terrestrial mammals, including for example humans, domestic pets, and livestock and other farm animals.

The following examples are offered for purposes of illustration, and are not intended to limit nor to define the invention. All literature citations in these examples and throughout this specification are incorporated herein by references for all legal purposes to be served thereby.

Materials and Methods for Examples 1 Through 11

A. Organ Culture Model and Measurement of Barrier Function

Timed pregnant Sprague-Dawley rats (plug date=day 0) were obtained from Simonsen (Gilroy, Calif., USA) and fetuses were delivered prematurely on day 17. Transepidermal water loss (TEWL) was measured in excised full-thickness flank skin from the fetal rats after various times in culture. The skin explants were placed dermis-side down onto collagen membrane inserts (3$\mu$ pore size) in medium M-199 (serum-free), and submerged, and the lateral edges and dermal surface were sealed with petrolatum, such that water loss occurred only through the epidermal surface. Explant samples were weighed hourly, at ambient temperature (24±3° C.) and humidity (40±5%), over 6 hours using a Cahn balance (sensitivity 0.001 mg). TEWL levels are reported as milligrams of water lost per square millimeter of epidermal surface per hour.

The compounds used in these examples are as follows:
farnesol
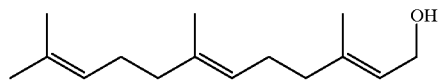
juvenile hormone III
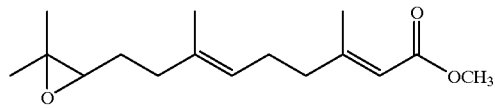
linoleic acid
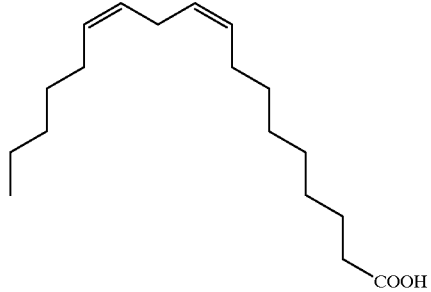
oleic acid
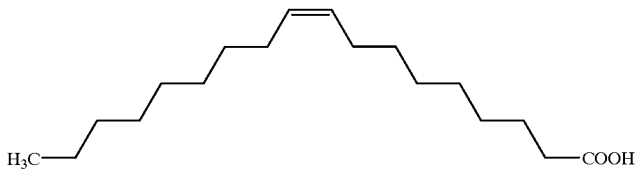
clofibrate
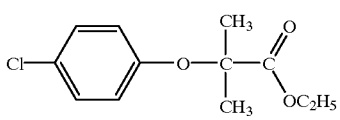
WY 14,643 (pirinixic acid)
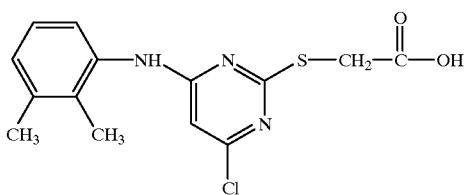
5,8,11,14-eicosatetraynoic acid (ETYA)
troglitazone
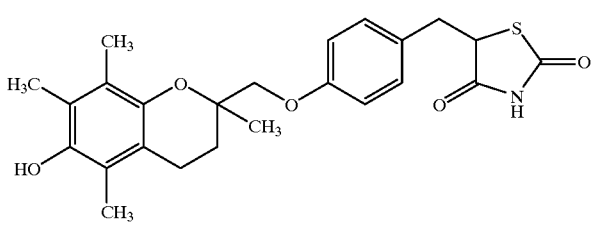
retinoic acid
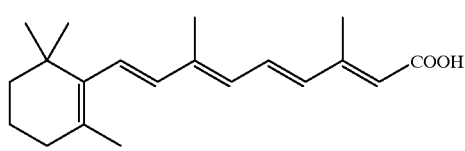

-continued
9-cis retinoic acid
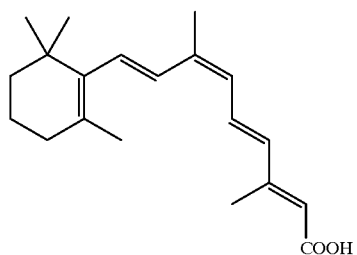
1,25-dihydroxy vitamin D
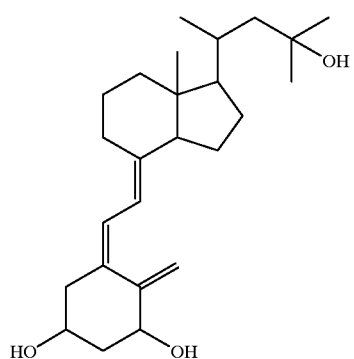
prostaglandin J2
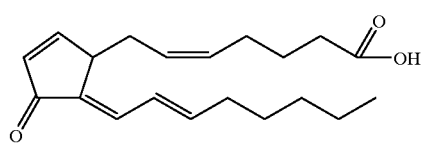
nerolidol
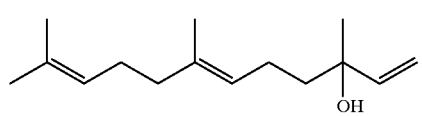
geranylgeraniol
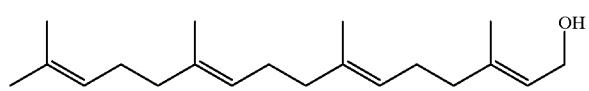
cis,trans-farnesol
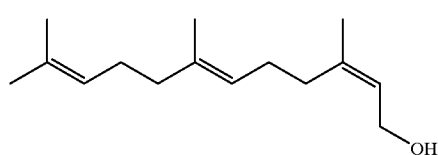
cholesterol
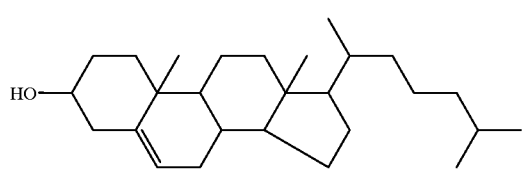
25-hydroxycholesterol
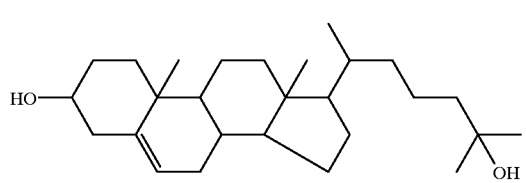

-continued

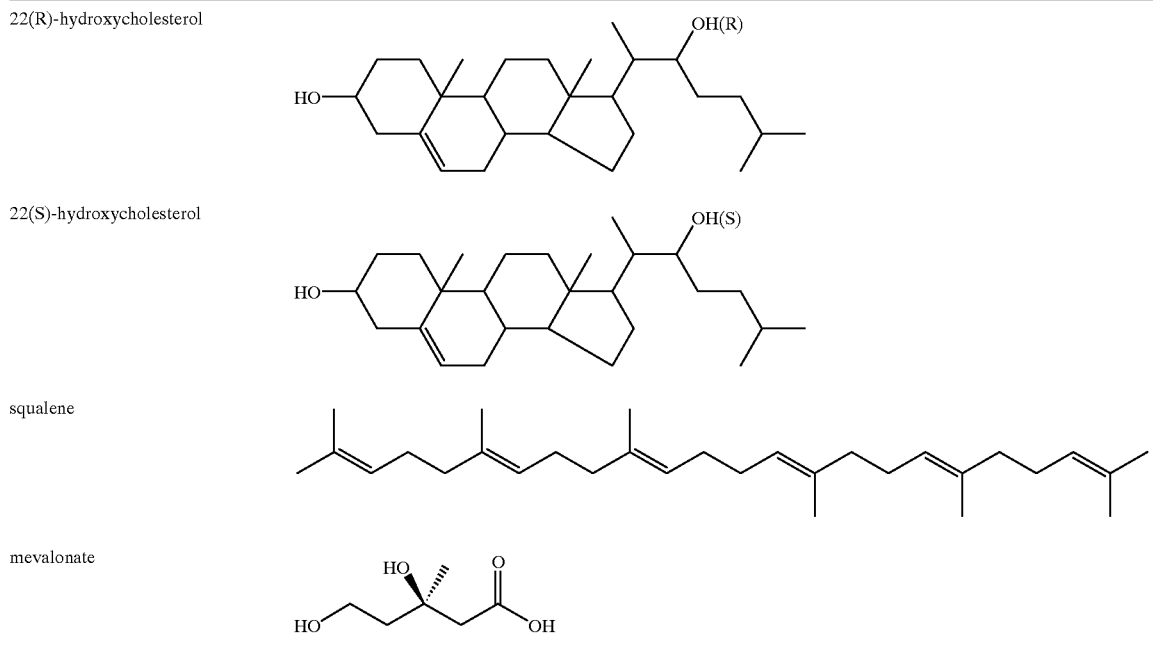

22(R)-hydroxycholesterol

22(S)-hydroxycholesterol squalene mevalonate

Prostaglandin J2 was obtained from Cayman Chemical Company (Ann Arbor, Mich., USA). Troglitazone was obtained from Parke-Davis Laboratories (Detroit, Mich., USA). The compound (4-chloro-6-(2,3-xylidino)-2-pyrimidinyl)thioacetic acid (known both as pirinixic acid and WY 14,643) were obtained from Wyeth Laboratories, Philadelphia, Pa., USA). The compounds cis-farnesol, nerolidol, and geranylgeraniol were obtained from University of California, Los Angeles, Calif., USA. All other compounds were obtained from Sigma Chemical Company (St. Louis, Mo., USA).

Fatty acids and clofibrate (p-chlorophenoxyisobutyric acid) were added to the medium bound to 0.5% (weight/volume) bovine serum albumin (BSA). Isoprenoids and oxysterols were added in ethanol ($\leq$0.1%) and juvenile hormone III was added as a dimethylsulfoxide (DMSO) solution ($\leq$0.1%). Control explants were incubated in the presence of the appropriate vehicle ($\leq$0.1% DMSO or ethanol, and/or $\leq$0.5% BSA).

B. Light and Electron Microscopy

Samples for light microscopy were fixed in modified Karnovsky's solution, plastic-embedded, and 0.5 $\mu$m sections were stained with toluidine. Samples for electron microscopy were minced into 1 mm$^3$ pieces, fixed in modified Karnovsky's fixative, and processed. Sections were stained with uranyl acetate and lead citrate, post-fixed in ruthenium tetroxide, and examined using a Zeiss 10A electron microscope.

C. Tissue Preparation for Enzyme Assays

Epidermis was separated from dermis after incubation in 10 mM ethylenediamine tetraacetic acid (EDTA) in Ca$^{++}$- and Mg$^{++}$-free phosphate-buffered saline (PBS), pH 7.4, at 37° C. for 30–40 minutes. The tissues were then minced, and homogenized on ice (three times at 15 seconds each with a Polytron homogenizer, followed by sonication twice at ten seconds each at 35% power) in either PBS containing 0.1 mM phenylmethylsulfonyl fluoride (PMSF) and 0.1% Triton X-100 (for β-glucocerebrosidase) or in 10 mM Tris (pH 7.5) containing 0.15 M sucrose and 2 mM EDTA (for steroid sulfatase). β-Glucocerebrosidase activity was measured in the supernatant following centrifugation at 10,000×g for fifteen minutes at 4° C. Steroid sulfatase activity was measured in the microsomal fraction resulting from a 10,000×g centrifugation (10 minutes, 4° C.) followed by 60 minutes of 100,000×g ultracentrifugation at 4° C. Protein content was measured by conventional techniques.

D. β-Glucocerebrosidase and Steroid Sulfatase Activities

β-Glucocerebrosidase activity was assayed using the synthetic substrate 4-methylumbelliferyl β-D-glucoside (4-MUG). The assays were performed in 5 mM sodium taurocholate in citrate-phosphate buffer (pH 5.6) with 0.5 mM 4-MUG for sixty minutes at 37° C., with a final assay volume of 100 $\mu$L, and protein concentration of 1–2 mg/mL. The reaction was terminated with 2 mL of carbonate-bicarbonate buffer (pH 10.5). The fluorescence was then measured at 360 $\lambda$ (excitation) and 450 $\lambda$ (emission) and compared with a standard 4-methylumbelliferone (4-MU) curve.

Steroid sulfatase activity was measured by incubating 100 $\mu$g of microsomal protein in 0.1 M Tris containing 5.6 mM glucose (pH 7.4) with 15 $\mu$M ($^3$H) dihydroepiandrosterone sulfate (DHEAS) (15 $\mu$Ci) in a final volume of 1.1 mL. The product, ($^3$H) DHEA, was extracted with benzene and an aliquot counted by scintillation spectrophotometry.

E. Statistical Analysis

Statistical evaluation was performed using a Student's test.

EXAMPLE 1

The experiments reported in this example demonstrate that not all activators of RXR heterodimers accelerate barrier development. Activators of three particular receptors—the retinoid receptor, the vitamin D receptor, and the peroxisome proliferator-activated receptor γ (PPARγ)—were used, and the negative results are demonstrated.

Prior studies have shown that full-thickness skin from gestational day 17 rats, after two days in culture, exhibits lamellar bodies in the granular cells and lamellar material secreted in the stratum corneum interstices, but, like day 19 rat skin in utero, the epidermis lacks mature lamellar membrane structures and a competent barrier. Hanley, K., et al., "Epidermal barrier ontogenesis: maturation in serum-free media and acceleration by glucocorticoids and thyroid hormone but not selected growth factors," *J. Invest. Denmatol.* 106:404–411 (1996). In contrast, a stratum corneum with barrier function equivalent to that observed in mature epidermis normally forms by day 4 in culture, corresponding to day 21 in utero. Hanley et al. (1996).

Skin explants from gestational day 17 rats were incubated in the presence of either various activators or vehicle, and transepidermal water loss was measured after two days. The activators and the concentrations at which they were used were as follows:

9-cis-retinoic acid: an activator of the retinoid X receptor (RXR); concentration 1 $\mu$M all-trans-retinoic acid: an activator of the retinoic acid receptor (RAR); concentration 1 $\mu$M 1,25-dihydroxyvitamin D3: an activator of the vitamin D receptor; concentration 1 $\mu$M prostaglandin J2: an activator of PPAR$\gamma$; concentration 10 $\mu$M The results in terms of trans-epidermal water loss (TEWL) are shown in bar-graph form as the top four bars in FIG. 1, which when compared with the control (the bottom bar in the Figure) indicate that none of these four activators had any significant effect on reducing the TEWL and hence promoting the barrier development.

In further tests, whose results are not shown in FIG. 1, the first three activators were tested at concentrations ranging from 1 nM to 1 $\mu$M, for their effect on the rate of barrier development. No effect was seen at any concentrations tested within this range.

These data demonstrate that activators of the retinoid receptors, vitamin D receptor and PPAR$\gamma$ do not accelerate fetal barrier development.

EXAMPLE 2

The experiments reported in this example demonstrate that activators of PPAR$\alpha$ accelerate barrier development, while activators of other PPAR subtypes do not.

Linoleic acid is an example of an activator of PPAR$\alpha$, and the TEWL value for explants incubated in 300 $\mu$M linoleic acid for two days is shown in FIG. 1. In contrast to the four ineffective activators discussed in Example 1 and the control, all of which are also shown in FIG. 1, linoleic acid markedly decreased the TEWL (p<0.005, n=8).

The three PPAR subtypes presently known are PPAR$\alpha$, PPAR$\delta$, and PPAR$\gamma$. These subtypes are pharmacologically distinct and differentially activated by various agents. Yu, V. C., et al., "RXR$\beta$: a coregulator that enhances binding of retinoic acid, thyroid hormone, and vitamin D receptors to their cognate response elements," *Cell* 67:1251–1266 (1991). To determine whether barrier development acceleration is attributable specifically to PPAR$\alpha$, a variety of PPAR activators were tested, as follows:

oleic acid: an activator for PPAR$\alpha$ and suspected of also being an activator for PPAR$\delta$, tested at a concentration of 300 $\mu$M ETYA: an activator for PPAR$\alpha$ and suspected of also being an activator for PPAR$\delta$, tested at a concentration of 100 $\mu$M WY 14,643: an activator for PPAR$\alpha$ only, tested at a concentration of 100 $\mu$M clofibrate: an activator for PPAR$\alpha$ only, tested at a concentration of 300 $\mu$M troglitazone: an activator for PPAR$\gamma$ only, tested at a concentration of 10 $\mu$M Also relevant to this study is the test result for prostaglandin J2, an activator for PPAR$\gamma$ only, which is shown in FIG. 1.

Figure 2:
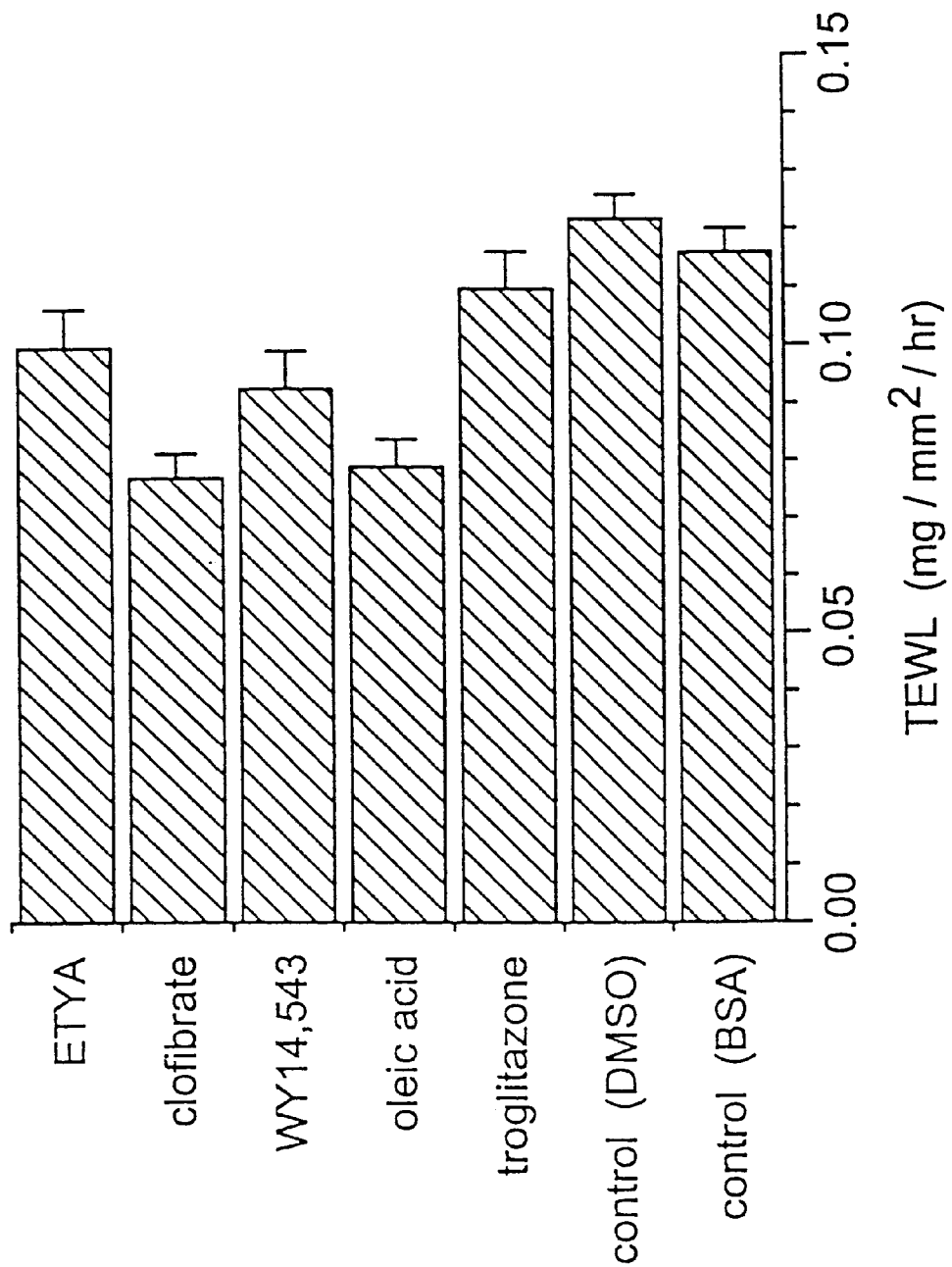
FIG. 2 is a bar graph showing TEWL test results of five additional compounds, three of which are within the scope of this invention.

The results of the five activators listed above are shown in bar-graph form in FIG. 2, where two controls are included. All activators of PPAR$\alpha$, including those known to activate only PPAR$\alpha$ demonstrated a significant positive effect, whereas the PPAR$\gamma$ activator troglitazone (like the PPAR$\gamma$ activator prostaglandin J2 shown in FIG. 1) had no effect. These results indicate that activators of PPAR$\alpha$ accelerate barrier development while activators that activate only PPAR$\gamma$ do not accelerate barrier development.

EXAMPLE 3

The experiments reported in this example demonstrate that activators of farnesol X-activated receptor (FXR) accelerate barrier development, while other compounds that are either similar in structure to farnesol, metabolites of farnesol, metabolic precursors of farnesol, or other metabolites of metabolic precursors of farnesol, do not accelerate barrier development.

Referring again to FIG. 1, farnesol is included in the bar graph, which lists the TEWL value for explants incubated in 50 $\mu$M farnesol for two days. In contrast to the four ineffective activators discussed in Example 1 and the control, farnesol markedly decreased the TEWL (p<0.005, n=8) to a similar degree as did linoleic acid.

To determine whether the effect on barrier development by farnesol is mediated by FXR, several other compounds related to farnesol in the ways stated or by similarly being known to activated FXR were tested for TEWL. Farnesol is produced by a multi-step metabolic synthesis from acetyl coenzyme A, and one of the key intermediates is mevalonate. As part of the pathway, mevalonate is converted in a rate-limiting step to isopentenyl pyrophosphate which through a series of reactions converts to farnesyl pyrophosphate. The latter is converted directly to farnesol but is also capable of following separate pathways toward the synthesis of compounds such as cholesterol, ubiquinone, dolichol, carotenoids, vitamin D, bile acids and steroid hormones. The farnesol pathway in turn leads to farnesoid metabolites such as farnesal, farnesoic acid, methyl farnesoate, and juvenile hormone III.

This series of experiments therefore included tests on mevalonate (tested at 200 $\mu$M), juvenile hormone III (at 100 $\mu$M) and 25-hydroxy cholesterol (at 50 $\mu$M), as well as nerolidol (at 100 $\mu$M), geranylgeraniol (at 50 $\mu$M), cis-farnesol (at 50 $\mu$M), and squalene (at 50 $\mu$M), due the similarities in structure between the latter four compounds and farnesol.

Figure 3:
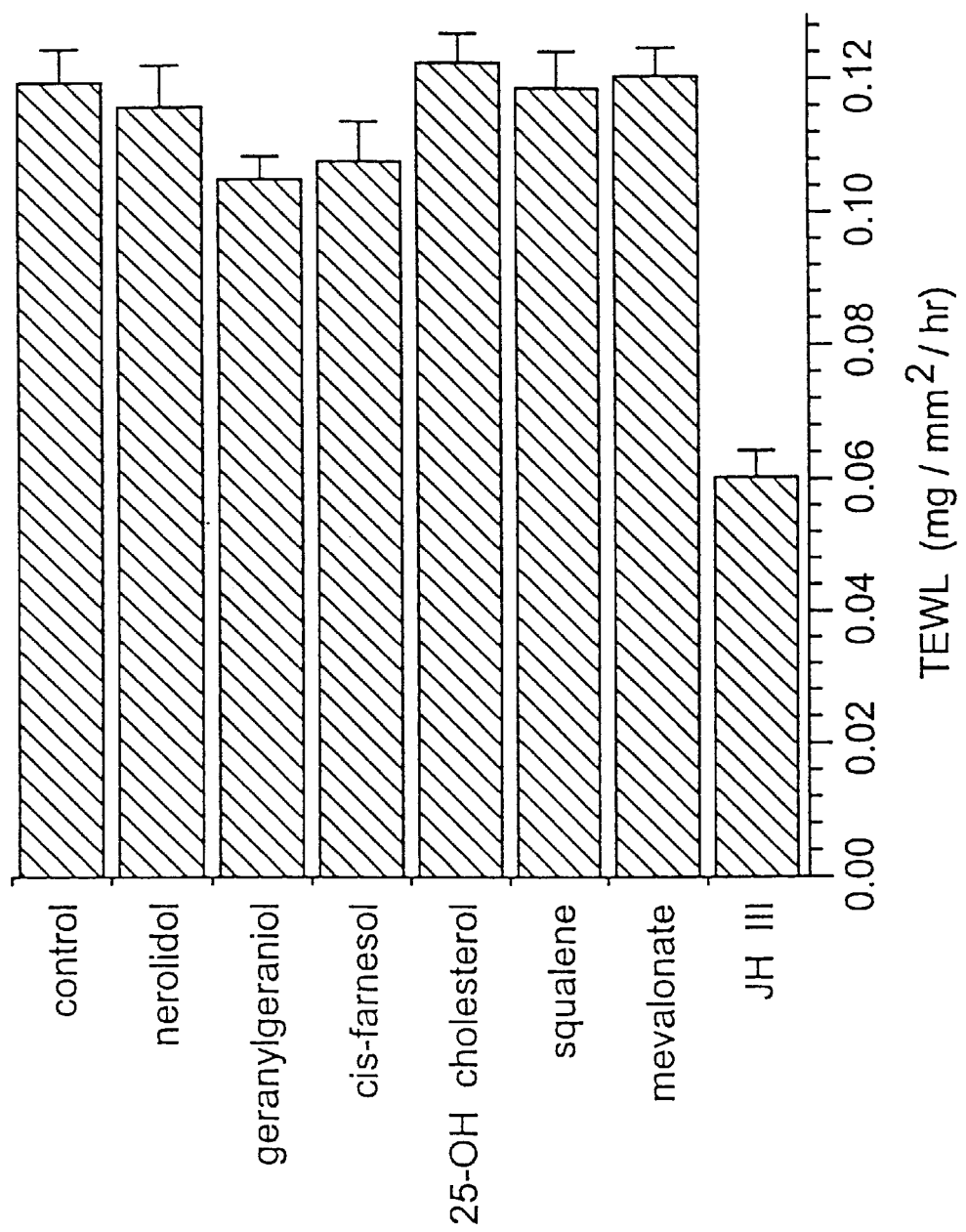
FIG. 3 is a bar graph showing TEWL test results of seven additional compounds, one of which is within the scope of this invention.

The results of these tests are shown in the bar graph of FIG. 3, which indicates that juvenile hormone III at 100 $\mu$M significantly accelerated barrier formation (p<0.005, n=6). By contrast, neither mevalonate at 200 $\mu$M, 25-hydroxy cholesterol at 50 $\mu$M, squalene at 50 $\mu$M, geranylgeraniol at 50 $\mu$M, cis-farnesol at 50 $\mu$M, nor nerolidol at 100 $\mu$M significantly affected barrier function. These results indicate that the acceleration of barrier development by farnesol and juvenile hormone III is FXR mediated.

EXAMPLE 4

The experiments reported in this example explore the dose responses of the various PPAR$\alpha$ and FXR activators tested in the preceding examples. Tests for TEWL were conducted as described above, using clofibrate, oleic acid, linoleic acid, farnesol and juvenile hormone III, each over a range of concentrations. The results are plotted in FIGS. 4a (clofibrate and oleic acid), 4b (linoleic acid) and 4c (farnesol and juvenile hormone III). For both clofibrate and oleic acid, maximal effects on barrier development occur at a concentration of approximately 500 $\mu$M, and half-maximal effects occur at approximately 250 $\mu$M. For linoleic acid, the maximal effect occurs at approximately 30 $\mu$M and the half-maximal effect at approximately 12.5 $\mu$M. Farnesol demonstrated a maximal effect at approximately 50 $\mu$M and a half-maximal effect at approximately 20 $\mu$M. Juvenile hormone III demonstrated a maximal effect at approximately 250 $\mu$M and a half-maximal effect at approximately 75 $\mu$M.

EXAMPLE 5

A series of experiments was performed to determine whether activation of both RXR and FXR, or both RXR and PPAR$\alpha$ would result in barrier development to a greater degree than activation of FXR or PPAR$\alpha$ alone, either in a synergistic or additive manner.

Explants were incubated in 9-cis-retinoic acid in combination first with clofibrate, then with farnesol, then with both, followed by measurements of TEWL. The 9-cis-retinoic acid was tested at a concentration of 1 $\mu$M, while the clofibrate and farnesol were both tested at suboptimal concentrations as determined in Example 4 above—i.e., clofibrate at 100 $\mu$M and farnesol at 10 $\mu$M. No effect on either function or epidermal morphologic maturation was observed by either combination.

Experiments were then performed to determine whether the combination of a PPAR$\alpha$ activator and an FXR activator would produce a synergistic result or an additive result. A first set of experiments was performed using suboptimal concentrations of these two activators (clofibrate at 100 $\mu$M and farnesol at 10 $\mu$M). The results are plotted in the bar graph of FIG. 5a, where they are compared with a control (no activators present). The TEWL value for clofibrate, represented by the bar labeled "Clo," is identical to the data point in FIG. 4a at the same concentration, while the TEWL value for farnesol, represented in FIG. 5a by the bar labeled "Farn," is identical to the data point in FIG. 4c at the same concentration. The TEWL value for the combination of the two activators is represented in FIG. 5a by the bar labeled "Clo+Farn," and shows that barrier development was significantly accelerated, indicating an additive effect of clofibrate and farnesol.

Figure 4A:
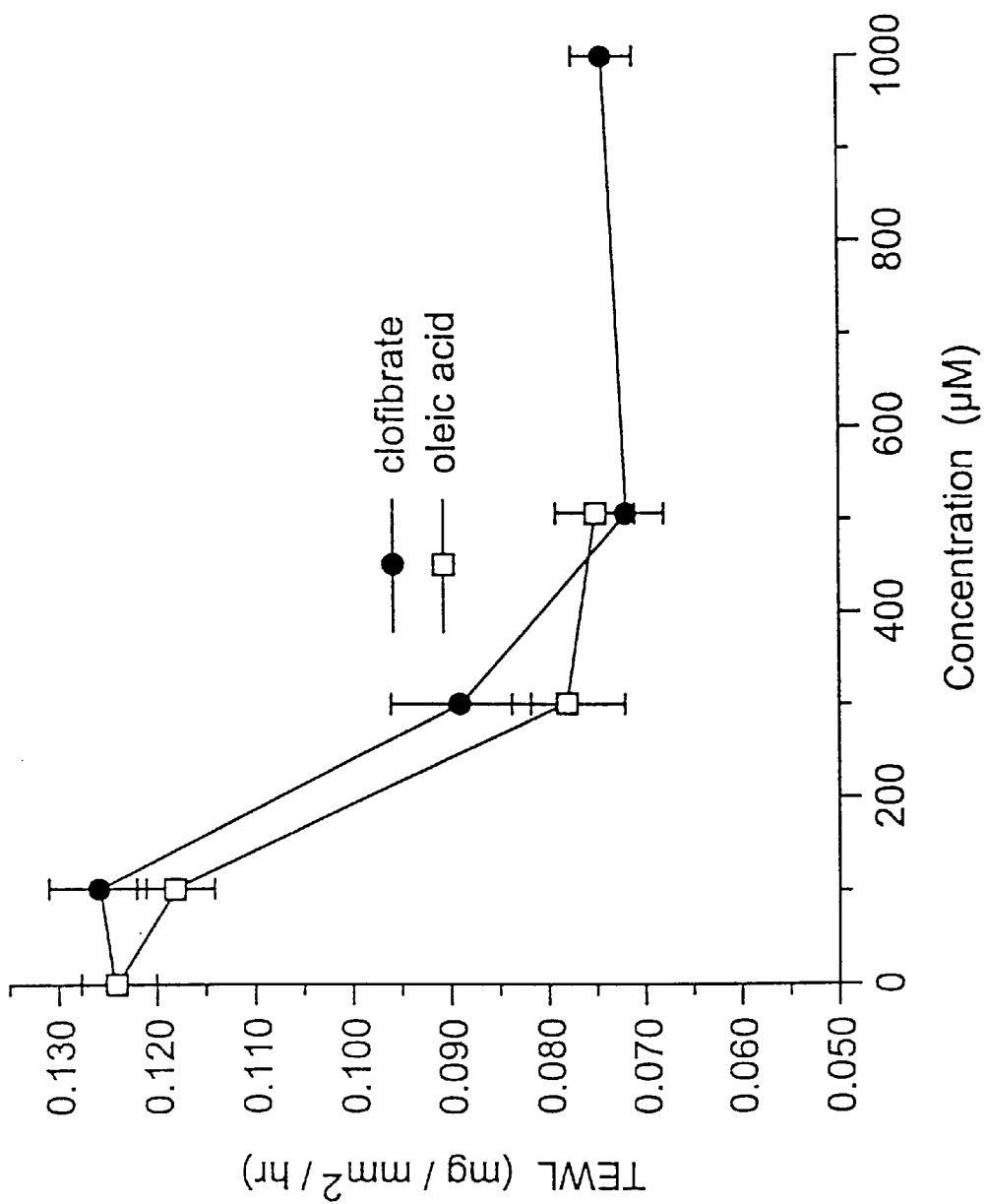
FIG. 4a is a plot of TEWL vs. concentration of active ingredient for two compounds within the scope of this invention.
Figure 4B:
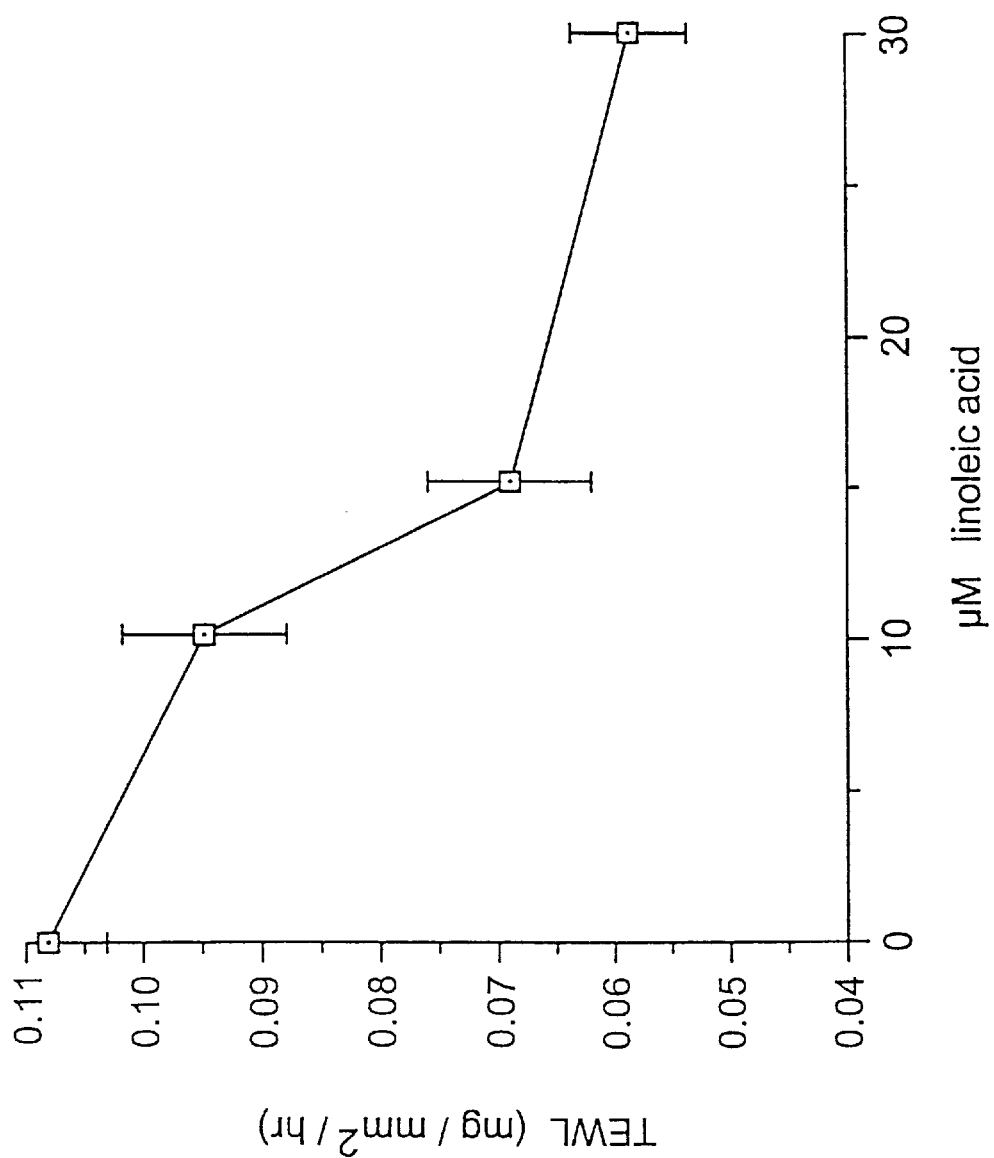
FIG. 4b is a plot of TEWL vs. concentration of active ingredient for a third compound within the scope of this invention.
Figure 4C:
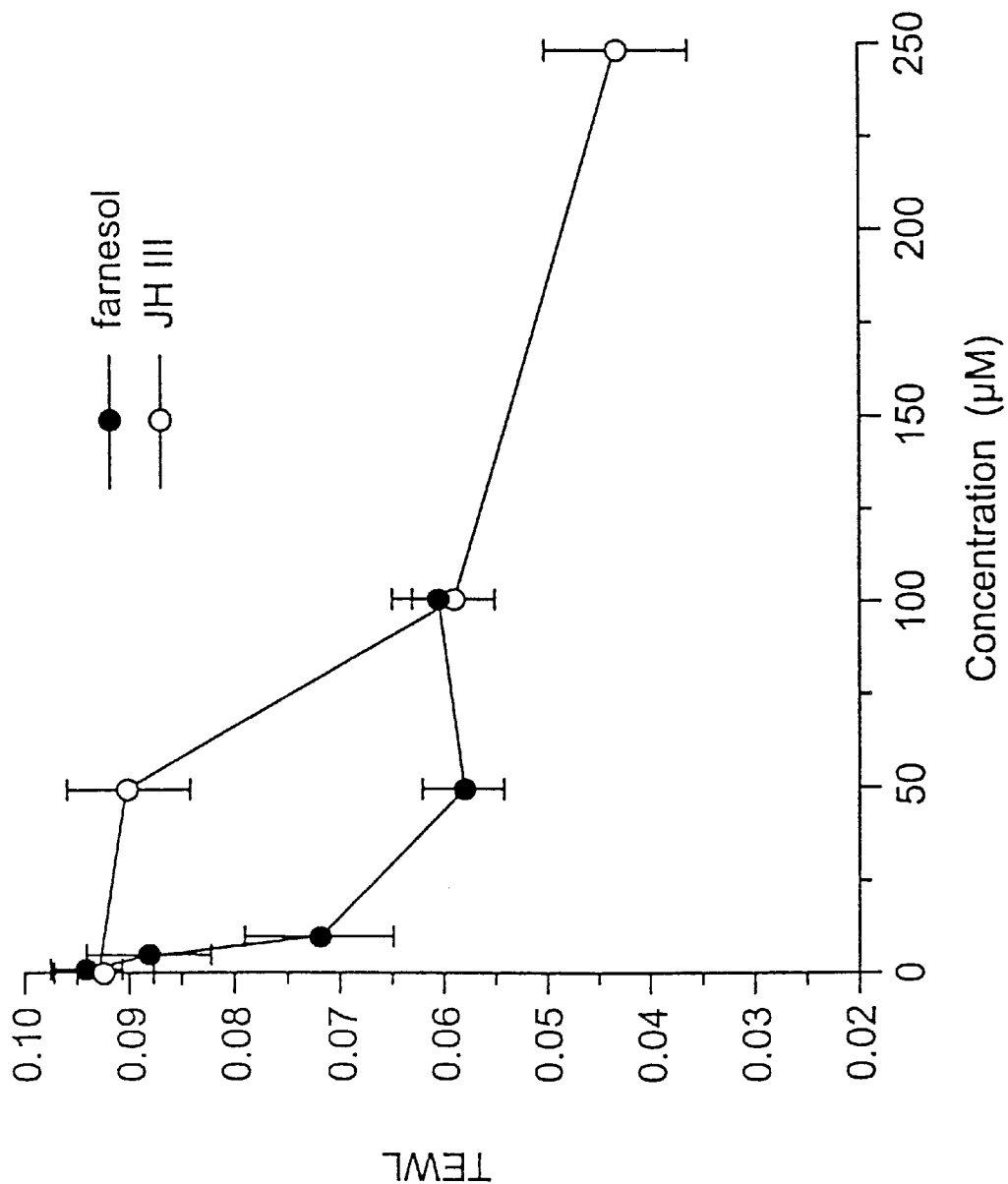
FIG. 4c is a plot of TEWL vs. concentration of active ingredient for a fourth compound and a fifth compound within the scope of this invention.
Figure 5A:
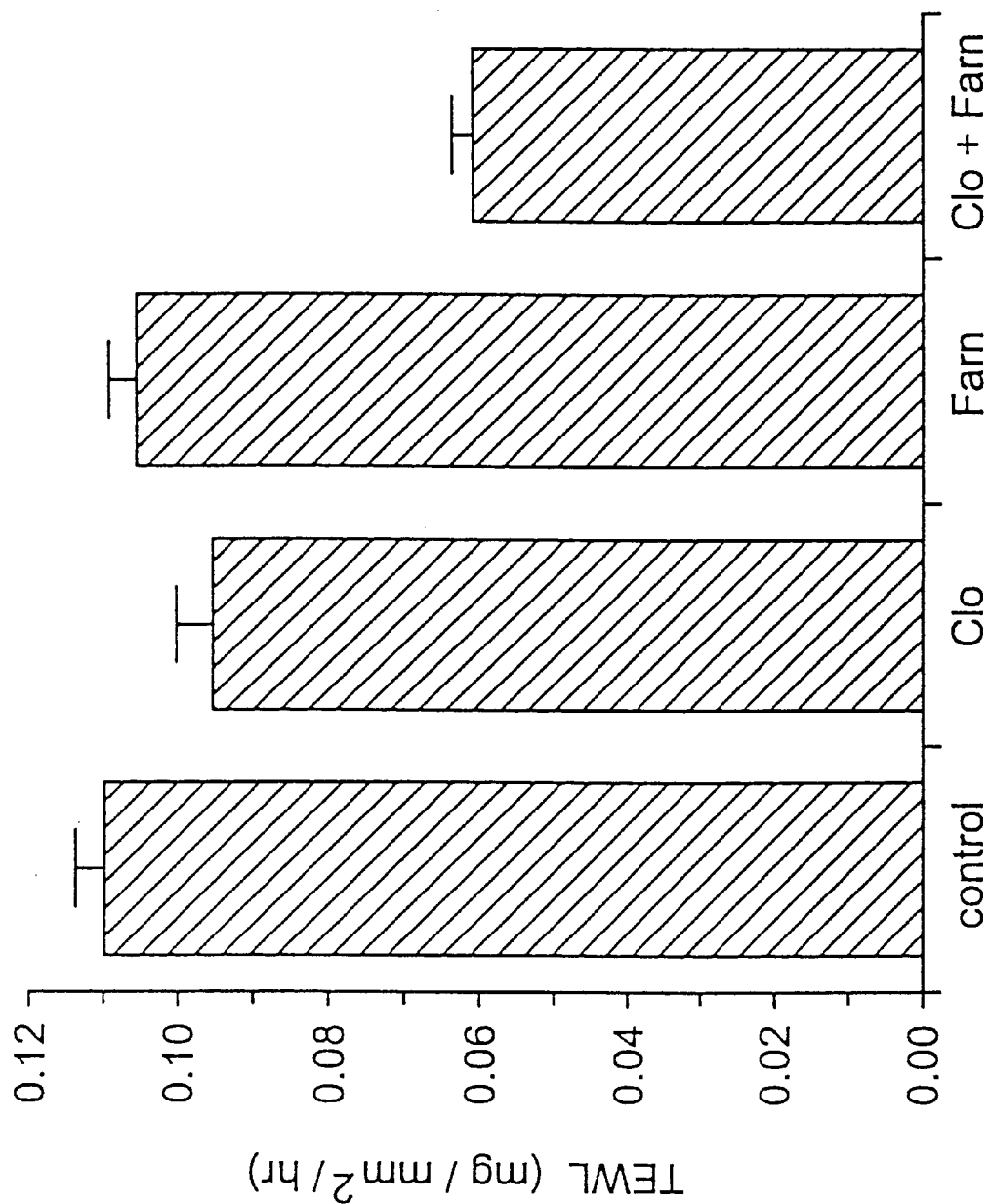
FIG. 5a is a bar graph showing TEWL test results for two compounds within the scope of this invention at suboptimal levels; both individually and in combination.
Figure 5B:
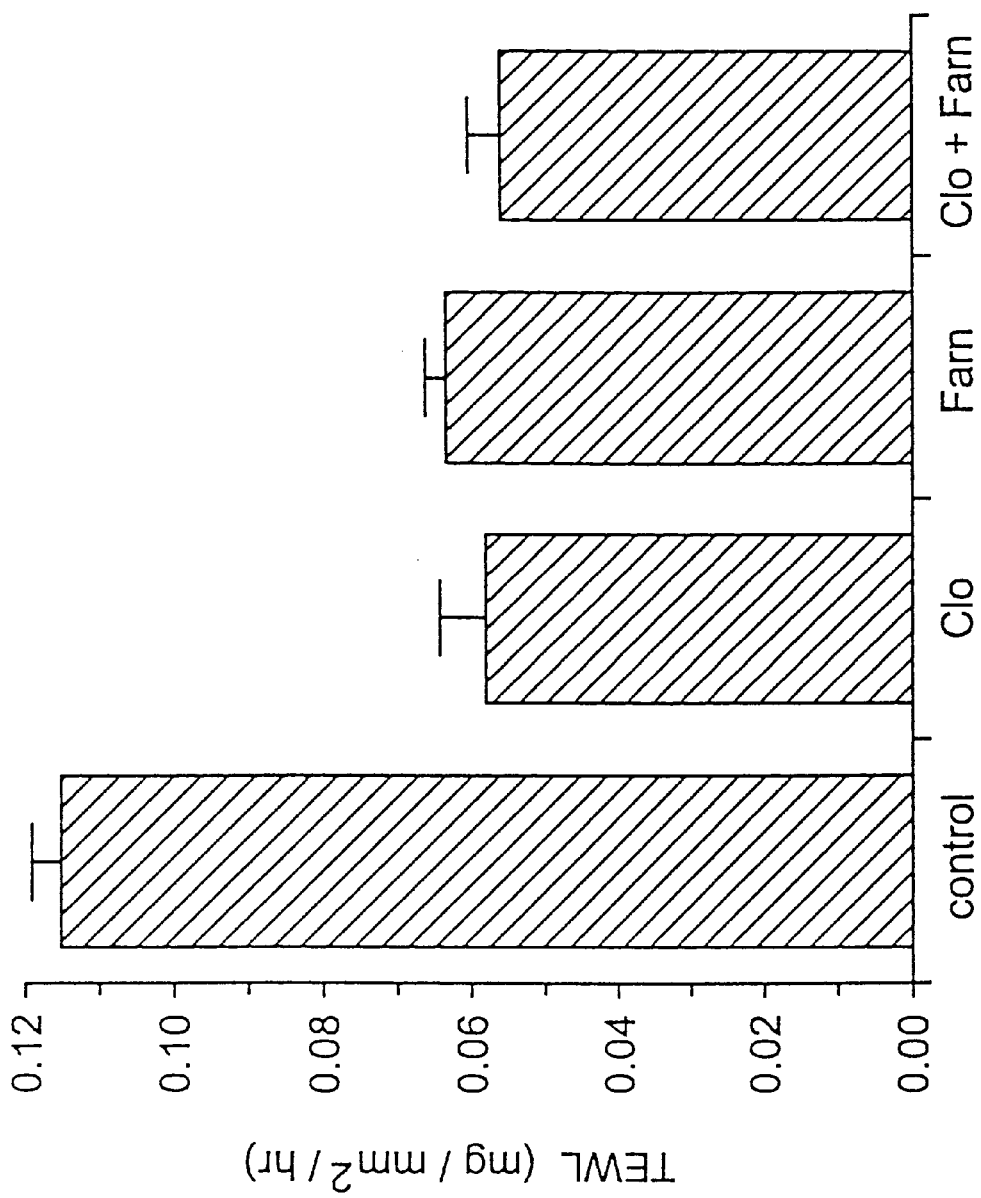
FIG. 5b is a bar graph showing TEWL test results for the same two compounds as FIG. 5a except at optimal levels, both individually and in combination.

In a second set of experiments, whose results are shown in FIG. 5b, farnesol and clofibrate were used at their maximal concentrations, as determined in FIGS. 4a and 4c. The TEWL value for clofibrate in FIG. 5b is represented by the bar labeled "Clo" and is identical to the value in FIG. 4a at the maximally effective concentration, while the TEWL value for farnesol is represented in FIG. 5b by the bar labeled "Farn" and is identical to the value in FIG. 4c at the maximally effective concentration. The TEWL value for the combination of the two activators at their maximally effective concentrations is represented in FIG. 5b by the bar labeled "Clo+Farn," and shows that barrier development was not further accelerated as compared to the values for the two activators alone.

The additive effects of clofibrate and farnesol at suboptimal doses suggest a similar activation pathway toward barrier development. This is further suggested by the lack of synergy in combining the same two activators at maximally effective concentrations. The lack of synergy between 9-cis-retinoic acid and either clofibrate or farnesol suggests either that the pathway toward barrier development is independent of RXR activation, or that sufficient endogenous RXR activators were present.

EXAMPLE 6

This example seeks to determine whether a relationship exists at the light microscope and electron microscope levels between the effects of PPAR$\alpha$ and FXR activators and epidermal maturation.

Explants incubated in various media were examined by light microscopy. The incubation media included control medium (containing no activators) and various media individually containing 300 $\mu$M clofibrate, 100 $\mu$M juvenile hormone III, 300 $\mu$M oleic acid, 30 $\mu$M linoleic acid, 50 $\mu$M farnesol, and various concentrations of 9-cis-retinoic acid, all-trans-retinoic acid, and 1,25-dihydroxy vitamin D3.

The light microscopy of the epidermis in the control explants showed that these explants lacked both a distinct stratum granulosum and a distinct stratum corneum. In contrast, the explants incubated for 48 hours in the clofibrate-containing medium, the juvenile hormone III-containing medium, the oleic acid-containing medium, the linoleic acid-containing medium, and the farnesol-containing medium all had both a multi-layered stratum granulosum and a stratum corneum. The explants incubated in the retinoic acid-containing media (both 9-cis and all-trans) and those incubated in the 1,25-dihydroxy vitamin D3-containing medium did not exhibit a distinct stratum corneum, and were morphologically indistinguishable from the controls.

Observations were then made of the ultrastructural maturation of the outer epidermis in explants that had been incubated in the various media and then post-fixed in ruthenium tetroxide. Media identical to those of the preceding paragraph were used, excluding the retinoic acid-containing and 1,25-dihydroxy vitamin D3-containing media. Explants treated with all media containing FXR and PPAR$\alpha$ activators showed multiple arrays of mature lamellar membrane unit structures filling the extracellular domains of the stratum corneum. In neither the controls, the vitamin D3, the all-trans-retinoic acid, nor the 9-cis-retinoic acid cultures, were the extracellular lamellae in the single-layered stratum corneum organized into mature lamellar membrane unit structures.

These results indicate that stimulation of the functional development of the barrier is accompanied by accelerated epidermal stratification and differentiation and the more rapid appearance of mature lamellar unit structures in the stratum corneum.

EXAMPLE 7

This example investigates the effect of PPAR$\alpha$ and FXR activators on the expression of certain enzymes whose activities increases during barrier formation. It is known in the art that epidermal $\beta$-glucocerebrosidase activity increases during stratum corneum and barrier development in the rat in utero and in vitro, that inhibition of this enzyme prevents normal barrier formation, and that this enzyme is required for barrier homeostasis (in vivo barrier function in adult). It has also been shown that hormones that accelerate epidermal barrier formation increase $\beta$-glucocerebrosidase activity in fetal skin explants. Steroid sulfatase activity is also known to increase during barrier formation, and is also stimulated by hormones that accelerate barrier formation.

β-Glucocerebrosidase and steroid sulfatase were thus selected as enzymes for this study.

Skin explants from 17-day fetal rats were incubated for 24 or 48 hours in media individually containing clofibrate (300 μM) and juvenile hormone III (100 μM), and control media. Enzyme activity was measured and the results are presented in Table I as the mean values of five determinations±SEM (standard error of the mean). All p values are ≦0.005 compared with controls of the same time period.

TABLE I

Enzyme Activity

| | Activity | |
|---|---|---|
| | β-Glucocerebrosidase (nmol/min/mg) | Steroid Sulfatase (pmol/h/mg) |
| 24-Hour Incubation: | | |
| Vehicle | 1.35 ± 0.22 | 5.99 ± 0.80 |
| Clofibrate | 2.97 ± 0.30 | 13.90 ± 1.10 |
| Juvenile Hormone III | 2.89 ± 0.20 | 12.55 ± 1.25 |
| 48-Hour Incubation: | | |
| Vehicle | 3.02 ± 0.45 | 8.75 ± 0.91 |
| Clofibrate | 5.35 ± 0.89 | 22.51 ± 2.60 |
| Juvenile Hormone III | 5.20 ± 0.62 | 18.23 ± 2.35 |

The data in this table indicate that β-glucocerebrosidase activity was approximately two-fold higher in treated explants than in controls after both 24 hours and 48 hours, and that steroid sulfatase activity was also increased 1.6 times over controls after 24 hours, and 2.5 times after 48 hours. These data demonstrate that both clofibrate and juvenile hormone III accelerate the developmental increases in activity of two lipid metabolic enzymes associated with the formation of a competent barrier.

EXAMPLE 8

This example illustrates that activators of PPARα induce differentiation in keratinocytes, the differentiation being part of the process of developing a mature epidermal barrier. Involucrin and transglutaminase (and their mRNA) were measured as indicators of differentiation, these two proteins being components of the ectoskeleton of the corneosites of cells of the stratum corneum. The PPARα activator tested was clofibrate.

Figure 6A:
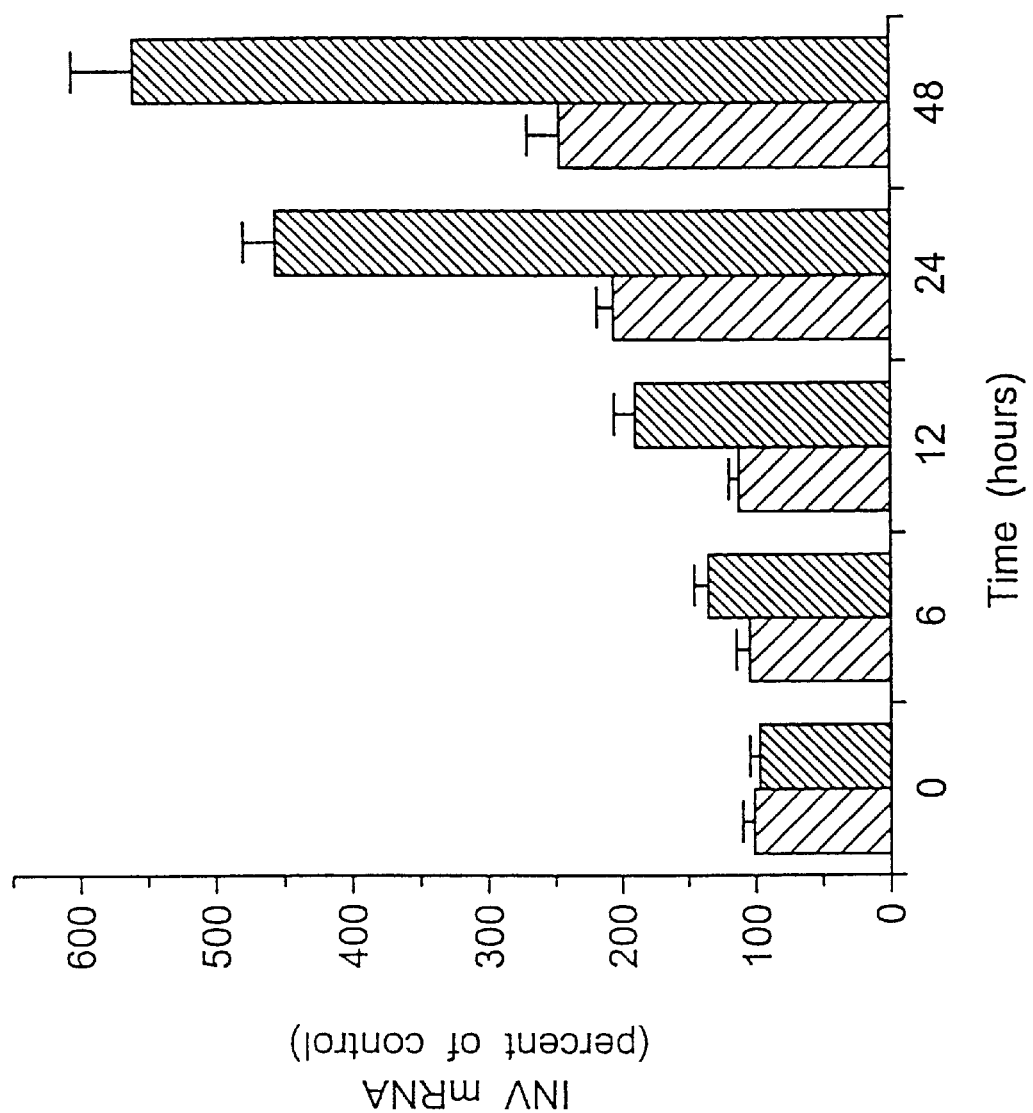
FIG. 6a is a bar graph showing levels of involucrin mRNA in cell cultures treated with clofibrate.
Figure 6B:
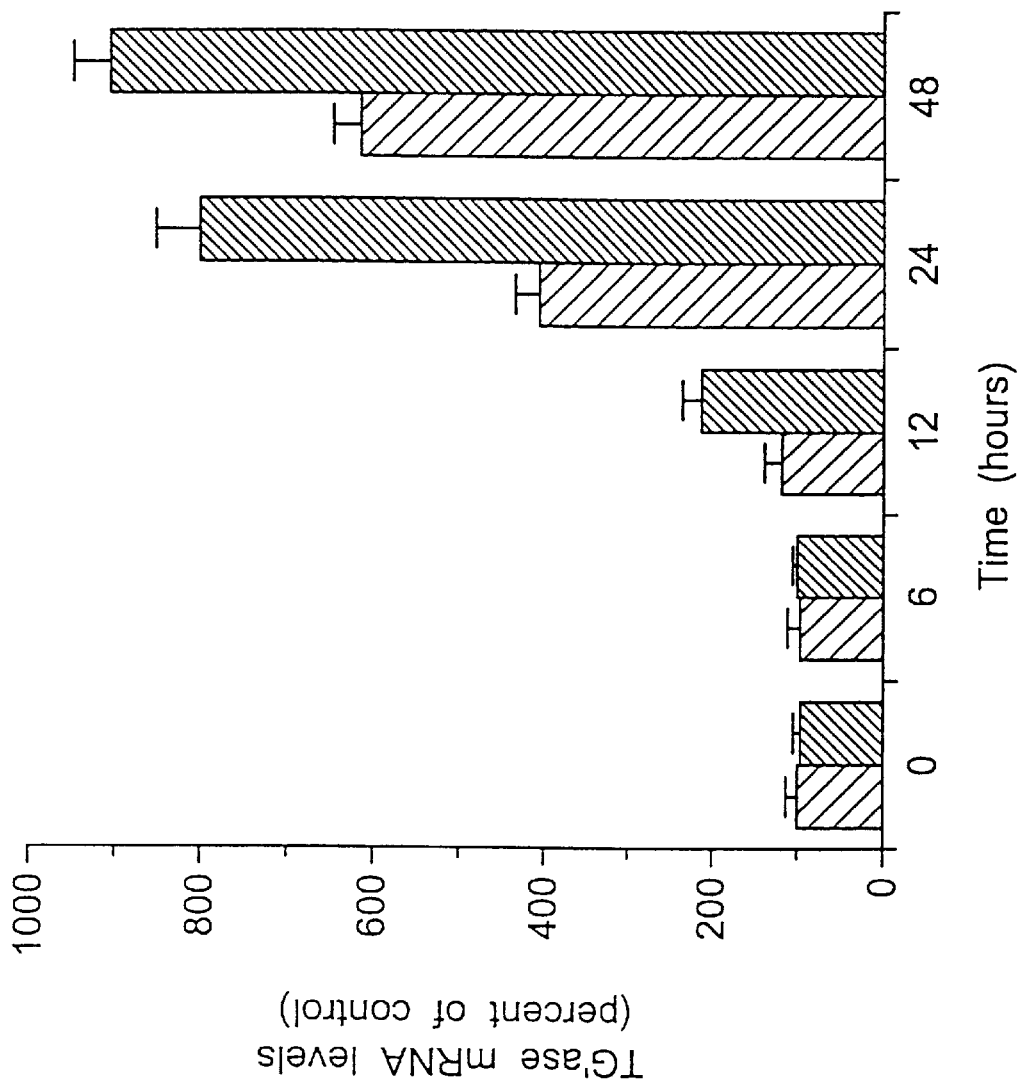
FIG. 6b is a bar graph showing levels of transglutaminase mRNA in cell cultures treated with clofibrate.

Human keratinocyte cells were incubated in culture containing calcium at a concentration of 0.03 mM $Ca^{++}$ (a level that is too low to induce differentiation). Also included in the culture medium were clofibrate at 400 μM or ETYA at 10 μM and 20 μM, while separate cell cultures were maintained as controls with neither clofibrate nor ETYA. The production of mRNA for both involucrin and transglutaminase was measured at intervals over a 48-hour time period (0, 6, 12, 24, and 48 hours) by Northern Blot analysis. The results for involucrin are shown in FIG. 6a and those for transglutaminase are shown in FIG. 6b. In each case, the lighter bars represent the control cells and the darker bars the cells incubated in the clofibrate-containing medium. The degree of mRNA generated is expressed as a percent of the control at zero hours. The data in the figures indicates that clofibrate-treated cells exhibit significantly increased levels of both involucrin beginning at six hours and transglutaminase beginning at twelve hours. Similar results were obtained with ETYA.

Figure 7A:
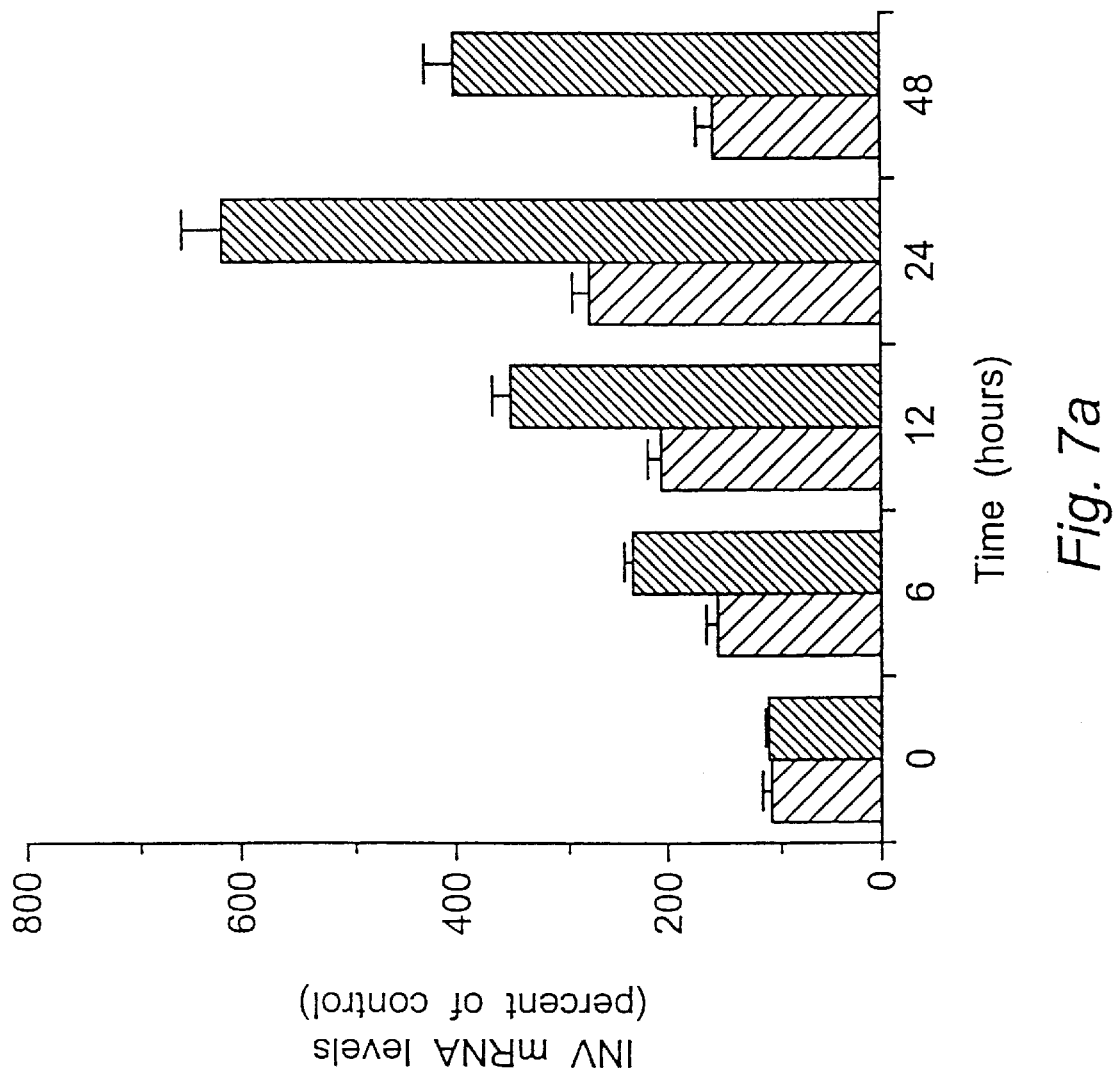
FIG. 7a is a further bar graph showing levels of involucrin mRNA in cell cultures treated with clofibrate.
Figure 7B:
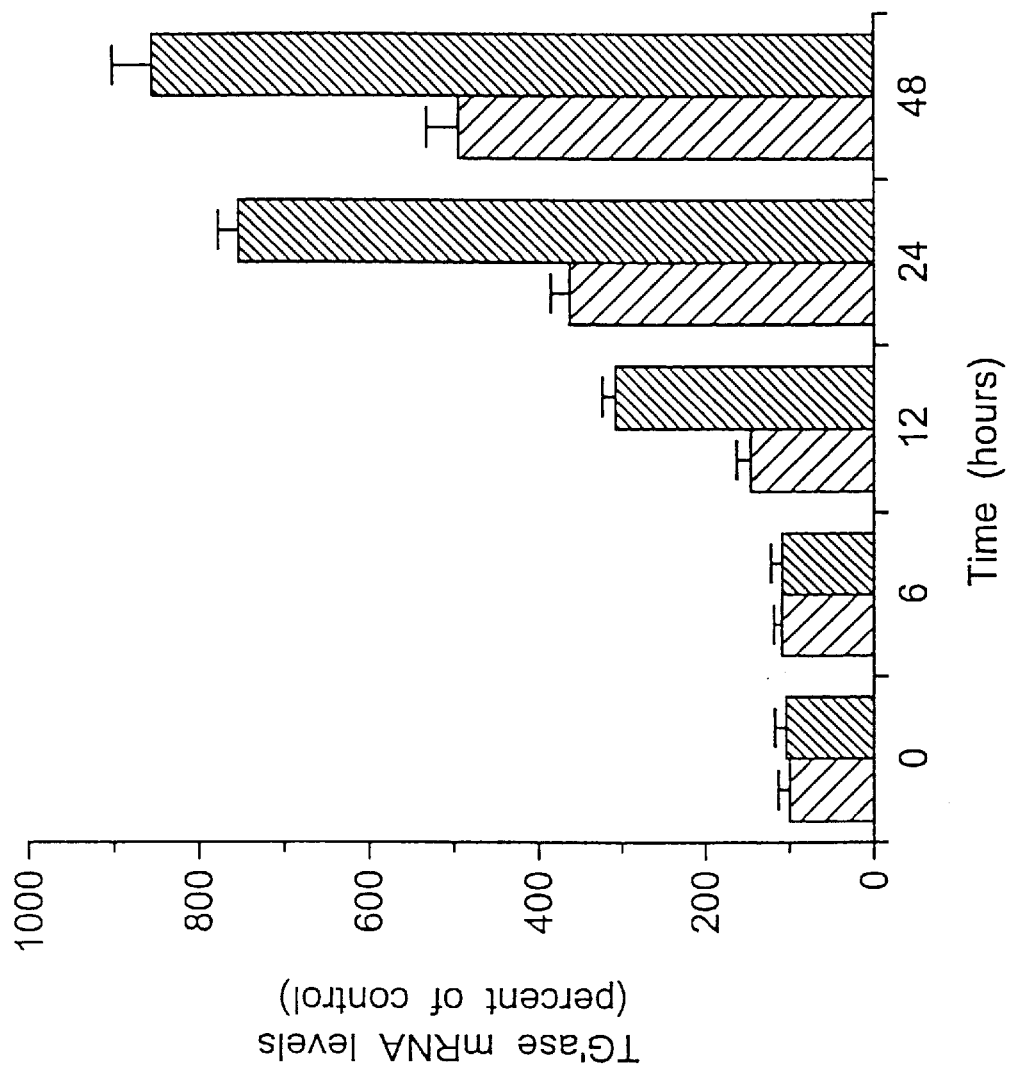
FIG. 7b is a further bar graph showing levels of transglutaminase mRNA in cell cultures treated with clofibrate. The calcium ion levels in the media represented by FIGS. 7a and 7b are higher than those of FIGS. 6a and 6b.

The experiments were then repeated, except with the calcium at a concentration of 1.2 mM $Ca^{++}$ in the media, a concentration high enough to induce differentiation by itself. The results for involucrin are shown in FIG. 7a and those for transglutaminase are shown in FIG. 7b. In these figures as well, the lighter bars represent the control cells and the darker bars the cells incubated in the clofibrate-containing medium, and the degree of mRNA generated is expressed as a percent of the control at zero hours. In the control cells, the involucrin mRNA level increases to a maximum at 24 hours, then declines by 48 hours, while the transglutaminase mRNA rises for the first 24 hours, then either levels off or continues to increase at a modest rate. The clofibrate-treated cells exhibit increased mRNA levels of both involucrin and transglutaminase at all time points relative to the controls. Similar results were obtained with ETYA.

Figure 8:
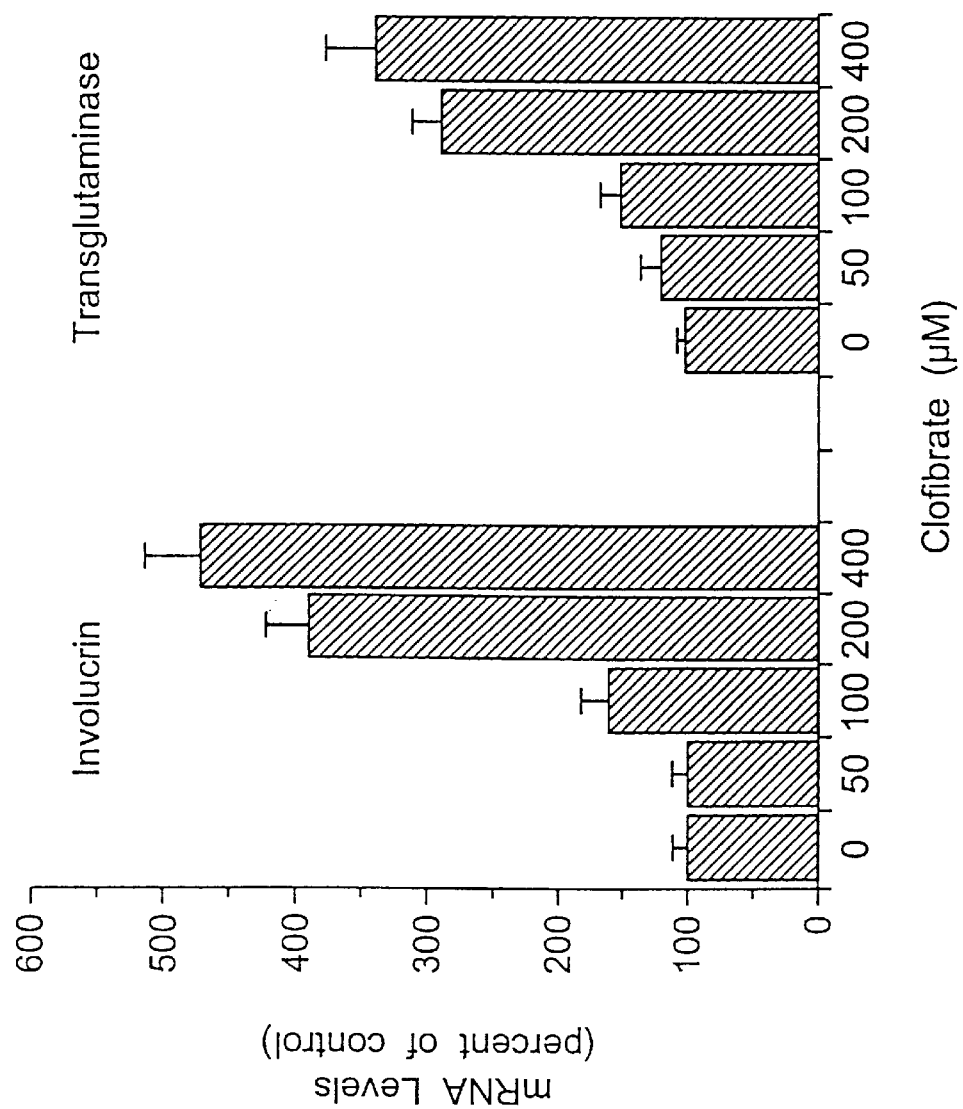
FIG. 8 is a bar graph showing levels of involucrin and transglutaminase mRNA in cell cultures treated with clofibrate at different doses.

The dose dependency of clofibrate on the levels of the two mRNAs was determined by a series of incubations for 24 hours using media containing varying concentrations of clofibrate ranging from 0 (vehicle only) to 400 μM, in either 0.03 mM or 1.2 mM $Ca^{++}$. The results in terms of both involucrin and transglutaminase mRNA levels are shown in FIG. 8, where the degree of mRNA generated is expressed as a percent of the respective measurements taken at zero hours. The mRNA levels for each protein are shown to increase with increasing dosages within this range.

Figure 9A:
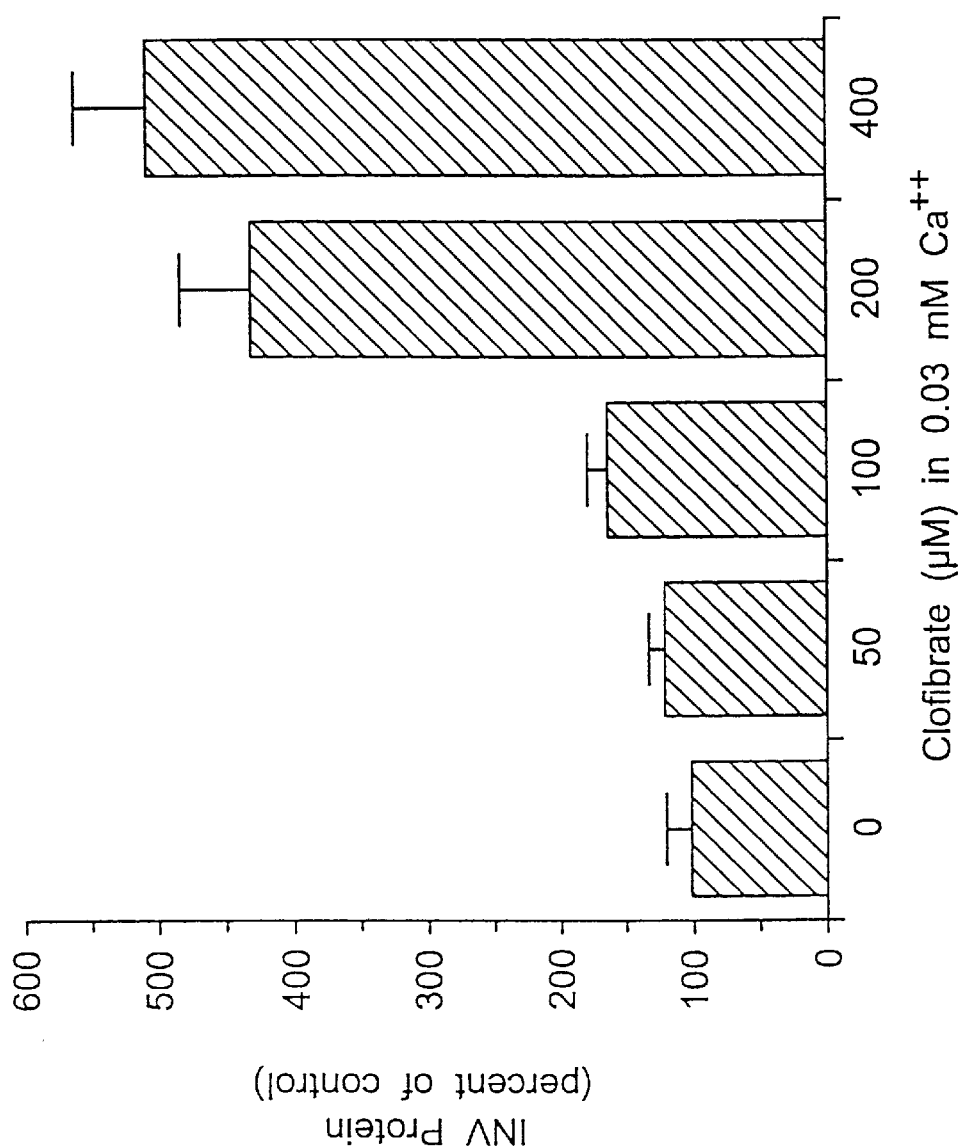
FIG. 9a is a bar graph showing levels of involucrin protein in cell cultures treated with clofibrate at different doses. Further 9b is a further bar graph showing similar data derived from media contaning a higher calcium content.
Figure 9B:
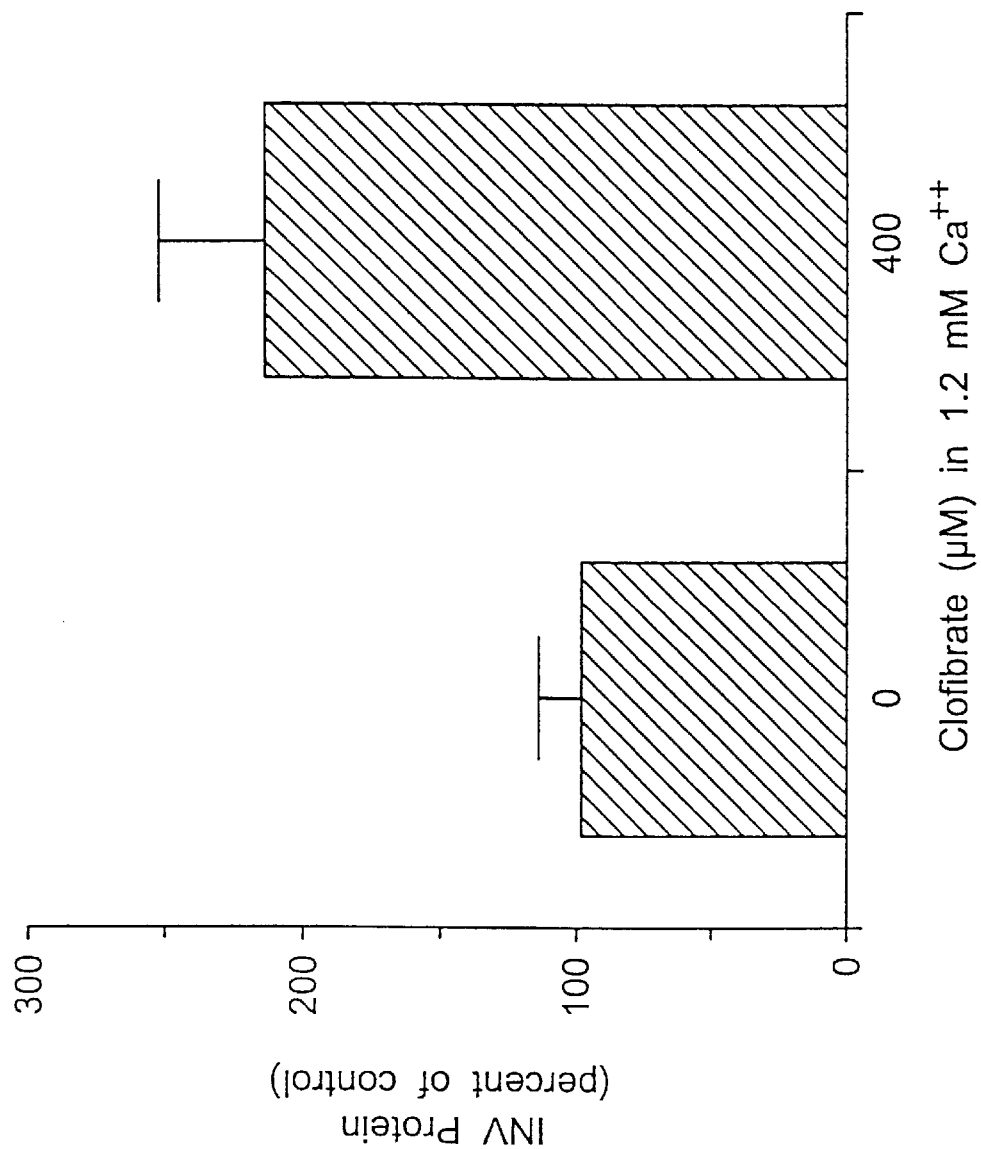

Measurements of the level of the involucrin protein itself were performed in the culture medium by Western Blot. Various incubations were performed, in media containing clofibrate at concentrations ranging from 0 (vehicle only) to 400 μM, and calcium ion at both 0.03 mM and 1.2 mM. The results are shown in FIG. 9a for tests with calcium ion at 0.03 mM, and in FIG. 9b for tests with calcium ion at 1.2 mM. In these figures, the protein contents are expressed as percents of the respective measurements taken from media incubated for the same period of time but in the absence of clofibrate. At both calcium levels, substantial increases in the protein content were observed as the clofibrate concentration was increased within this range. Together, these data demonstrate that PPARα activators have a profound effect on the expression of protein markers of epidermal differentiation.

EXAMPLE 9

This example demonstrates the increase in keratinocyte differentiation by FXR activators. This is an indication of increased expression of key protein markers of epidermal differentiation. The activators used were farnesol and juvenile hormone III.

Figure 10:
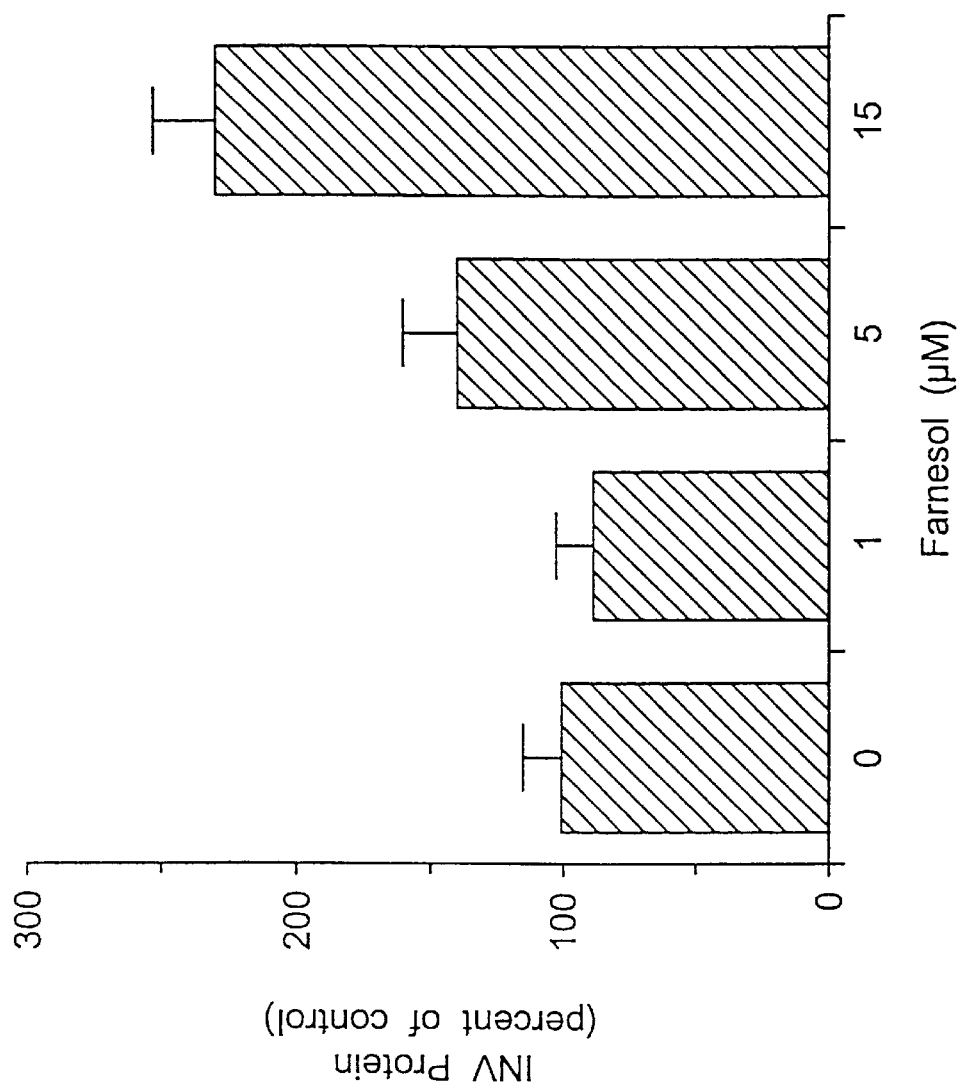
FIG. 10 is a bar graph showing levels of involucrin protein in cell cultures treated with farnesol at different doses.
Figure 11:
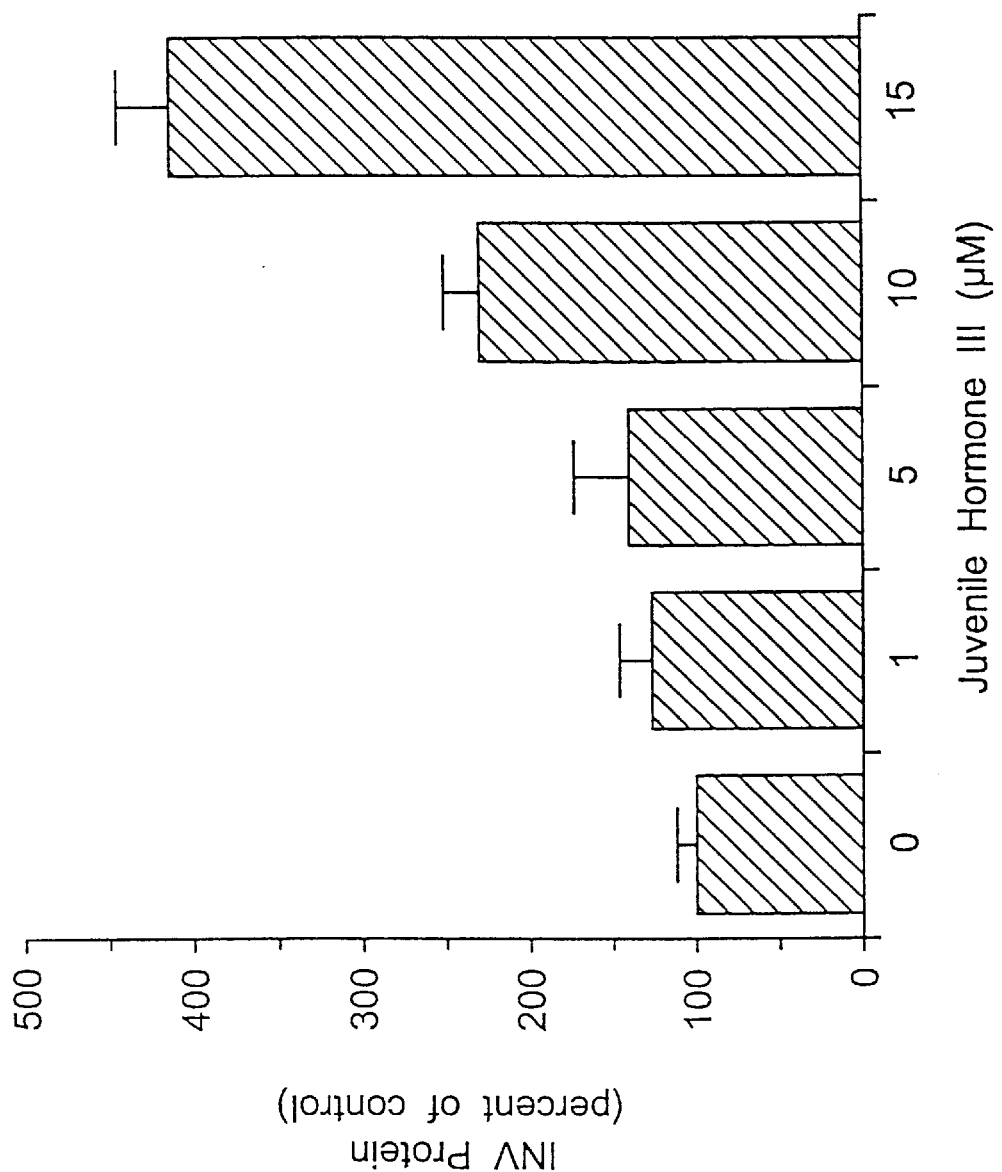
FIG. 11 is a bar graph showing levels of involucrin protein in cell cultures treated with juvenile hormone III at different doses.

The procedures of Example 8 were followed, and measurements were taken on the involucrin protein levels from cells incubated at various concentrations of farnesol and juvenile hormone III ranging from 0 (vehicle only) to 15 μM, in media containing 0.03 mM and 1.2 mM calcium ion, for 24 hours. The results are shown in FIG. 10 for farnesol and FIG. 11 for juvenile hormone III, in 0.03 mM $Ca^{++}$. The figures show substantial increases in involucrin protein content as the farnesol concentration was increased within this range, and the same was true for juvenile hormone III. These data show that FXR activators increase the expression of key protein markers of epidermal differentiation.

EXAMPLE 10

This example illustrates the effect of clofibrate, farnesol and juvenile hormone III on the rate of cornified envelope formation, as measured by $^{35}S$ incorporation into detergent- and reducing agent-insoluble protein.

Normal human keratinocytes were cultured to 80% confluence in KGM containing 0.07 $\mu$M $Ca^{++}$. At 80% confluence, the cells were switched to KGM containing 0.03 $\mu$M $Ca^{++}$ or 1.2 $\mu$M $Ca^{++}$, plus varying concentrations of clofibrate ranging from 0 to 400 $\mu$M. Cells were incubated in these solutions plus $^{35}$S-methionine/cysteine for 48 hours. Ionomycin, 5 $\mu$M, was added at 46 hours, two hours before assaying for cornified envelopes. Cells were rinsed with phosphate-buffered saline (PBS) and solubilized in 2% sodium dodecylsulfate, and an aliquot was placed in 4% sodium dodecylsulfate/40 mM dithiothreitol in boiling water for 30 minutes. The sodium dodecylsulfate-insoluble pellet was washed with 0.1% sodium dodecylsulfate/0.1% dithiothreitol, and the radioactivity incorporated into the detergent-insoluble cornified envelope was determined by scintillation counting. To determine total protein synthesized during the $^{35}$S-labeling period, an aliquot of cell lysate before boiling was precipitated with 10% trichloroacetic acid on ice for thirty minutes, washed with 5% trichloroacetic acid, and quantitated by scintillation counting. Percentage of cornified envelope was calculated as percentage cpm/total protein cpm×100.

The results are shown in Table II, where they are expressed as percent of the value representing the control with 0.03 mM $Ca^{++}$, and where each entry represents the mean±SEM of two independent experiments. For the data at 0.03 mM $Ca^{++}$ and 200 and 400 $\mu$M clifobrate, and for the data at 1.2 mM $Ca^{++}$ and 400 $\mu$M, the value of p was <0.01 relative to the corresponding vehicle-only controls.

TABLE II

Cornified Envelope Formation Induced by Clofibrate

| Calcium Content in Medium | Clofibrate Content in Medium | Cornified Envelope Formation (% of Control) |
|---|---|---|
| 0.03 mM | 0 | 100.0% ± 13.9 |
| 0.03 mM | 50 $\mu$M | 121.4% ± 15.7 |
| 0.03 mM | 200 $\mu$M | 321.3% ± 30.4 |
| 0.03 mM | 400 $\mu$M | 386.8% ± 28.7 |
| 1.2 mM | 0 | 488.0% ± 34.1 |
| 1.2 mM | 50 $\mu$M | 458.9% ± 39.8 |
| 1.2 mM | 200 $\mu$M | 529.3% ± 17.4 |
| 1.2 mM | 400 $\mu$M | 581.9% ± 28.7 |

The data in Table II indicate that clofibrate increased cornified envelope formation in both high and low $Ca^{++}$ media.

Figure 12:
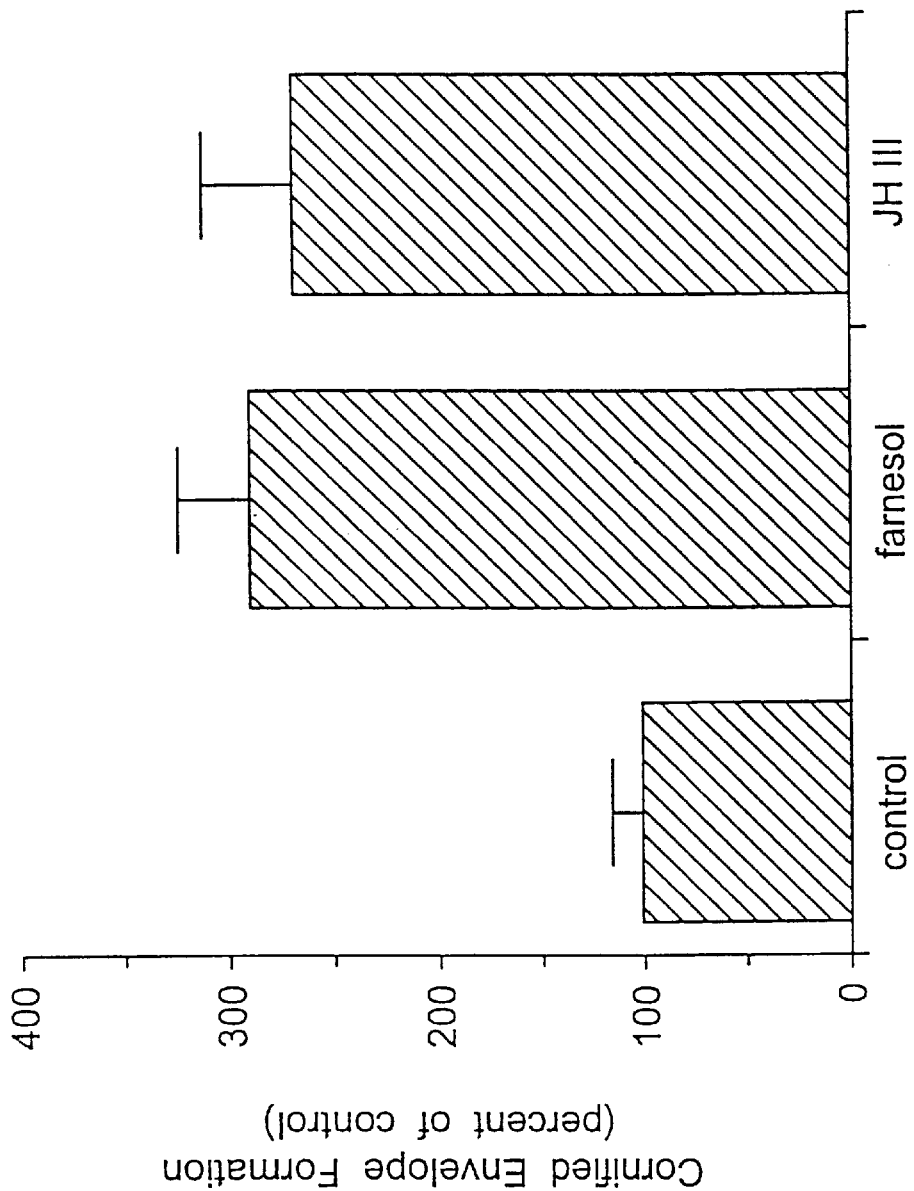
FIG. 12 is a bar graph showing levels of increase in the rate of cornified envelope formation in cell cultures treated with farnesol and juvenile hormone III at different doses.

Similar tests were performed using farnesol at 10 $\mu$M and juvenile hormone III at 15 $\mu$M, individually in separate media at low calcium concentration (0.03 mM). The 48-hour results are shown in FIG. 12, which indicates that both farnesol and juvenile hormone III produced substantial increases in the rate of cornified envelope formation.

EXAMPLE 11

This example illustrates the effect of clofibrate, farnesol and juvenile hormone II on keratinocyte cell growth, demonstrating that both PPARα and FXR activators inhibit cell growth and proliferation.

Preconfluent keratinocytes were treated for 48 hours with varying concentrations of clofibrate ranging from 0 (vehicle only) to 400 $\mu$M, in both low (0.03 mM) calcium and high (1.2 mM) calcium. The treated keratinocytes were harvested and sonicated, and the resulting homogenates were incubated with 1 $\mu$L/mL bis-benzimidazole for two hours in the dark. DNA content was quantified by reading the samples on a spectrofluorimeter. The results are shown in Table III. Each value in the table is a mean of three samples.

TABLE III

Effect of Clofibrate on Keratinocyte Growth

| Clofibrate ($\mu$M) | DNA Content After 48 Hours ($\mu$g/dish) | Significance |
|---|---|---|
| 0 | 15.5 ± 0.9 | — |
| 50 | 14.9 ± 1.5 | not significant |
| 200 | 12.9 ± 1.1 | p < 0.1 |
| 400 | 11.0 ± 1.3 | p < 0.01 |

Figure 13:
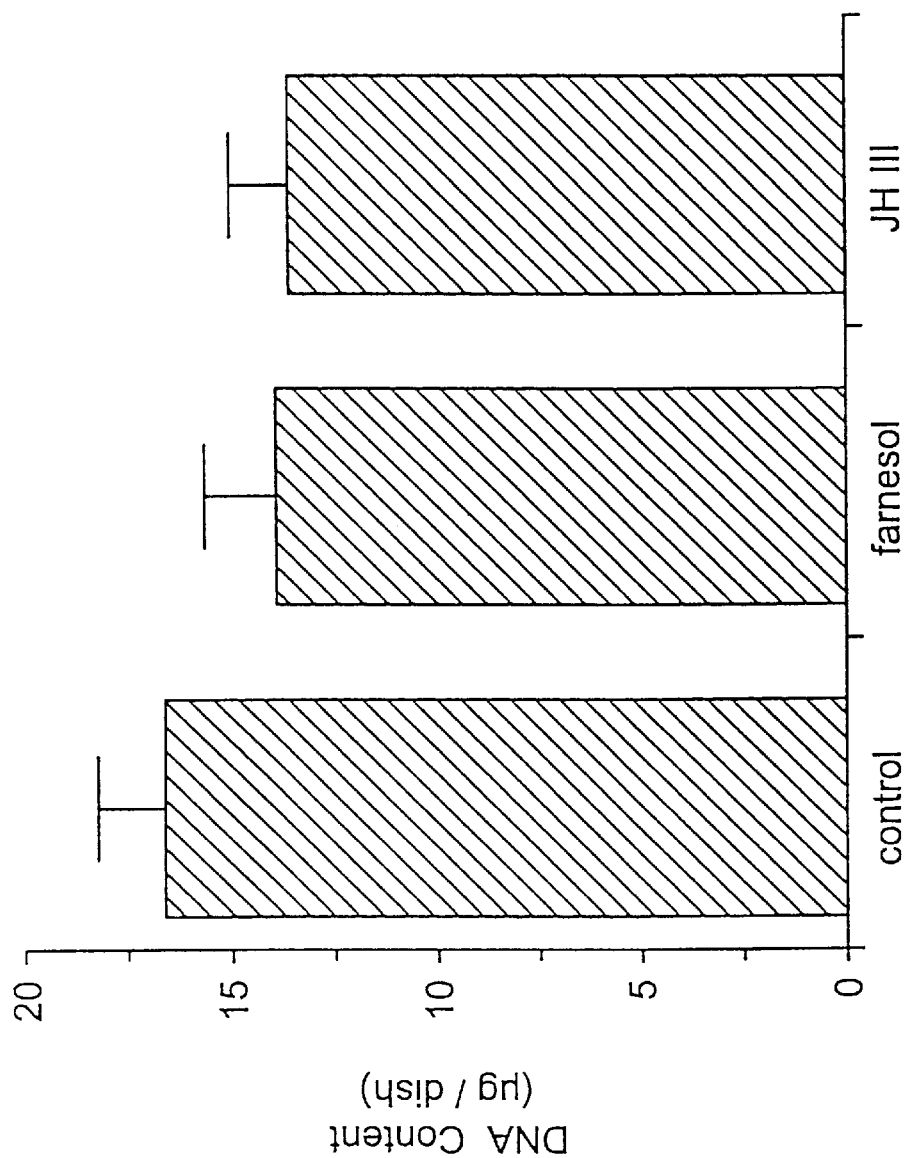
FIG. 13 is a bar graph showing the degree of decrease in DNA content in cell cultures treated with farnesol and juvenile hormone III at different doses.

Similar tests were performed using farnesol at 10 $\mu$M and juvenile hormone III at 15 $\mu$M, both in the presence of 0.03 mM $Ca^{++}$ and with 48 hours of incubation. The results are shown in FIG. 13. Table II and FIG. 13 collectively show that both PPARα and FXR activators inhibit cell growth.

Examples 12 through 17 address the activity of oxysterol activators of LXRα in the utilities addressed by this invention.

Materials and Methods for Examples 12 Through 17

A. Cell Culture

Human epidermis was isolated from newborn foreskins and keratinocytes were plated in serum-free keratinocyte growth medium ("KGM"; Clonetics, San Diego, Calif. USA), using conventional techniques. Cells were treated with either the test compounds in vehicle or vehicle alone (<0.1% ethanol) for 24 or 48 hours. The test compounds were obtained from Sigma Chemical Co. (St. Louis, Mo. USA) and were stored as 15 mM stock solutions at −20° C. Mevalonate was solubilized in sterile water.

B. RNA Isolation, Northern Blotting and cDNA Probes

Total RNA was isolated by using TRIZOL (Sigma Chemical Co.), following the manufacturer's protocol. Ethanol-precipitate RNA pellets were resuspended in sterile, diethylpyrocarbonate (DEPC)-treated water, and RNA was quantified by absorbance at 260 nm using the 260/280 nm ratio as an index of purity. RNA (15 $\mu$g per sample) was size fractionated through a 1% agarose gel containing 2.2 M formaldehyde. RNA integrity was visualized following acridine orange staining of the gel following electrophoresis. The RNA was transfered to a nylon membrane that was subsequently baked at 80° C. for 2 hours. Blots were hybridized with the appropriate $^{32}$P-labeled probe overnight at 65° C. Washes were then performed in a solution containing 0.1% SSC and 0.1% sodium dodecyl sulfate (SDS) for 20 minutes at room temperature, followed by a 20-minute wash at 65° C. Autoradiography was performed at −70° C. Blots were probed with β-actin to confirm equal loading. Appropriate bands were quantified by densitometry.

C. Involucrin and Transglutaminase Protein Levels

Protein concentration was assessed by protein electrophoresis and Western blotting. Cells were lysed in 2% SDS and the lysate sonicated. Protein determinations were made by use of a Bicinchoninic acid protein assay (Pierce Chemical Company, Rockford, Ill. USA). Following protein determination, equal amounts of protein (50 $\mu$g) were separated by electrophoresis on 7.5% polyacrylamide gels and electroblotted onto polyvinylidene difluoride membranes (0.2-$\mu$, obtained from Bio-Rad Laboratories, Hercules, Calif. USA). Involucrin protein was detected by incubation overnight at 4° C. with a polyclonal rabbit anti-human involucrin antibody (1:1000 dilution). The involucrin-specific bands on the autoradiograms were quantitated by densitometry. Transglutaminase protein expression was measured in a similar mmaner, using stacking, sample and running buffers containing 4 M urea, and the gels following electrophoresis were washed in 4 M urea, 25 mM TRIS-HCl, pH 7.4, 7.5 mM NaCl, 0.1 mM dithiothreitol (DTT), and 2 mM ethylenediamine tetraacetic acid for 90 minutes prior to electoblotting, allowing the transglutaminase to be detected by antibody. Specific bands on the autoradiograms were quantified by densitometry.

D. Cornified Envelope Formation

To determine the rate of cornified envelope formation, cells were labeled with $^{35}$S-methionine/cysteine (2 μCi/mL; trans $^{35}$S label, ICN Biomedical, Inc., Irvine, Calif. USA) for 48 hours, incubated for the last 2 hours with 5 μM ionomycin, washed with phosphate-buffered saline (PBS), and harvested into 1.1 mL of 2% SDS. Aliquots were reserved for protein determinations. The remaining cell lysate (1 mL) was sonicated briefly (10 seconds). One mL of 4% SDS/4 mM DTT was then added, and the mixture was heated to >95° C. for 30 minutes. The mixture was then cooled and SDS/DTT-insoluble material was collected on filter discs, washed with 0.5% SDS/0.5% DTT, and quantitated by scintillation spectrophotometry. To determine total protein synthesized during the 48 hours of $^{35}$S labeling, a reserved aliquot of the cell lysate (taken prior to heating) was precipitated with an equal volume of 2% bovine serum albumin (BSA) and 1 mL of 10% (weight/volume) trichloroacetic acid (TCA) on ice for thirty minutes, and $^{35}$S-labeled precipitated protein was collected onto filters (pore size P8, Fisher Scientific, Pittsburgh, Pa. USA), washed with 5% TCA, and quantified by scintillation spectroscopy. Total protein was determined by conventional methods.

E. DNA Synthesis

The rate of DNA synthesis was determined by measuring the incorporation of $^3$H-thymidine into cellular DNA after 16 hours of incubation with 2 μCi $^3$H-thymidine per mL of media (110 Ci/mmol methyl-1',2'-$^3$H-thymidine (Amersham Laboratories, Arlington Heights, Ill. USA). The cells were then solubilized in 1N NaOH, and the radioactivity in the washed TCA precipitate was quantitated by scintillation spectroscopy.

F. Transfections

Keratinocytes were transfected by passing primary keratinocytes onto 6-well multiwell plates 1–2 days prior to transfection to yield a confluence of 20–40% on the day of transfection. Involucrin promoter construct (1 μg), 0.1 μg RSV-β-gal, and 7.5 μg of polybrene (dihexabromide, Aldrich Chemical Company, inc., Milwaukee, Wis. USA) were added in media (KGM containing 0.03 mM Ca$^{++}$) in a final volume of 0.35 mL, and keratinocytes were incubated at 37° C. for 5 hours with gentle shaking each hour. Cells were then rinsed with CMF PBS, followed by incubation at room temperature for three minutes with 10% glycerol in media. Following two rinses with CMF PBS, keratinocytes were incubated overnight with 2 mL of KGM containing 0.03 mM Ca$^{++}$. Keratinocytes were treated the following day with fresh media (either 0.03 or 1.2 mM Ca$^{++}$) containing either 10 μM of the test compound of vehicle (ethanol). Cells were rinsed and harvested in 250 μL cell lysis buffer. The lysate was spun at 10,000×g (4° C.) for two minutes, and 20 μL of supernatant was assayed with luciferase substrate and β-galactosidase substrate. β-Galactosidase activity was used to normalize data and correct for any transfection inefficiencies.

EXAMPLE 12

This example demonstrates that the oxysterol activators of LXRα stimulate keratinocyte differentiation, as indicated by the levels of involucrin and transglutaminase mRNA, while cholesterol, mevalonate, and 22(S)-hydroxycholesterol demonstrated no significant effects.

Northern blot analyses were performed on keratinocytes maintained in low calcium (0.03 mM) and incubated for 24 hours in the presence of vehicle alone (<0.1% ethanol) or vehicle containing 25-hydroxycholesterol (10 μM), 22(R)-hydroxycholesterol (10 μM), cholesterol (10 μM), or mevalonate (500 μM) (individually). The mRNA levels of involucrin ("INV") and transglutaminase ("TG'ase") are shown in the bar graph of FIG. 14a, the INV indicated by clear bars and the TG'ase by shaded bars, both with error limits shown. The figure shows that both 25-hydroxycholesterol ("25-OH") and 22(R)-hydroxycholesterol ("22R-OH") exhibited an approximate twofold increase in mRNA levels compared to the vehicle alone. In contrast; neither cholesterol ("chol") nor mevalonate ("mev") had any effect.

Figure 14A:
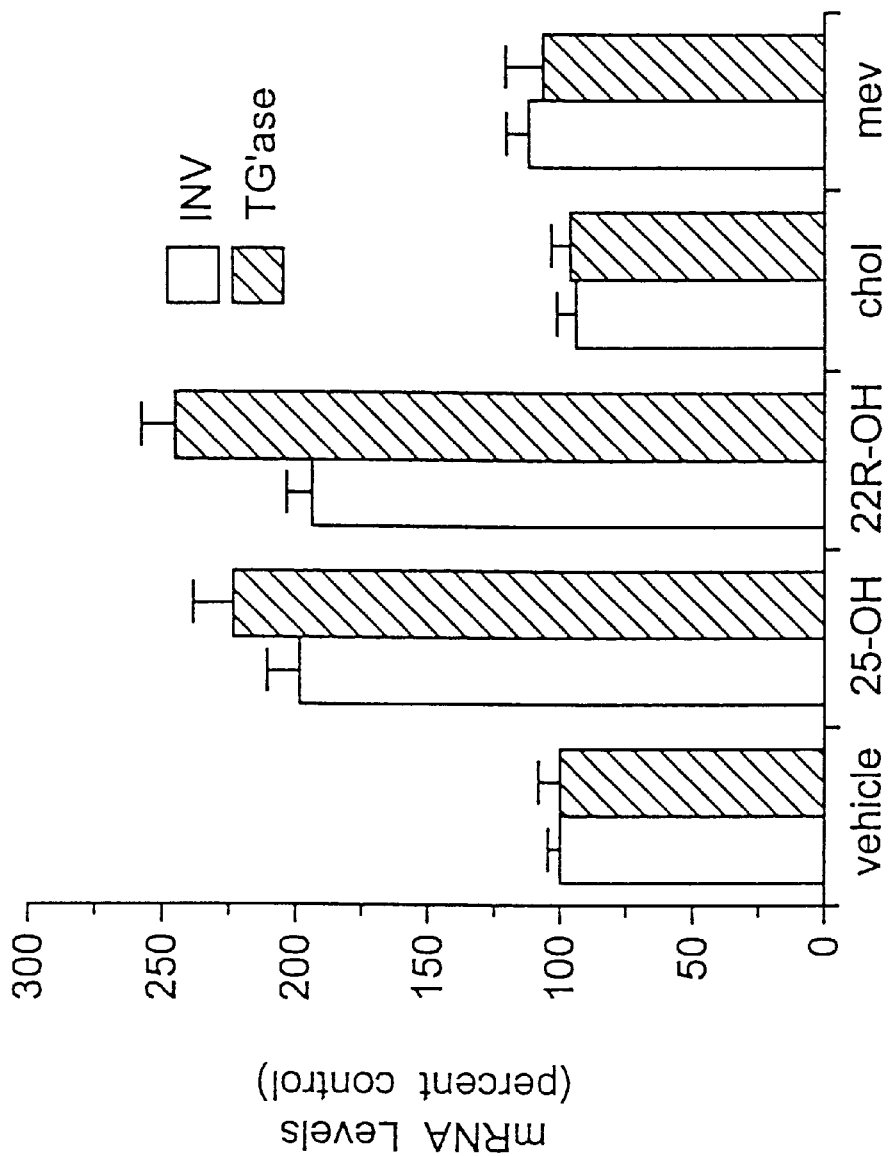
FIG. 14a is a bar graph showing levels of involucrin and transglutaminase mRNA levels in cell cultures treated with two LXRα activators as well as two related compounds (for comparison).
Figure 14B:
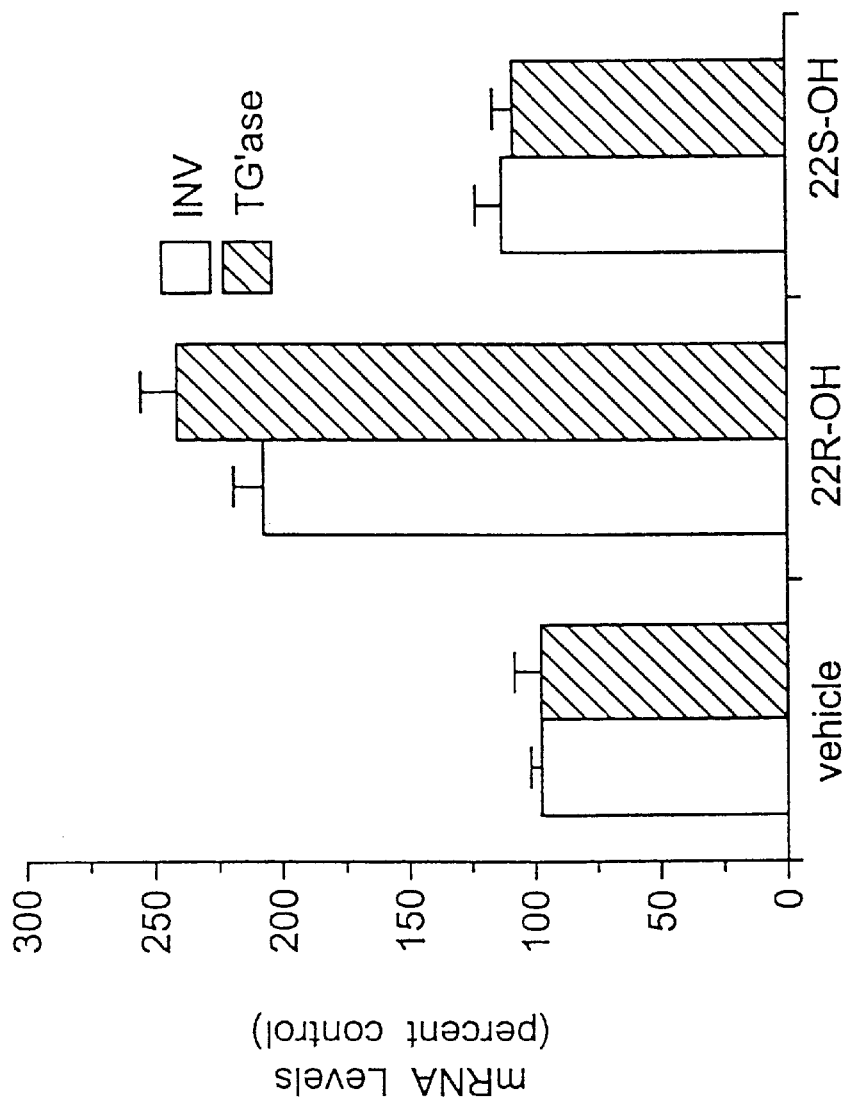
FIG. 14b is a bar graph with similar data and a comparison against a further related compound.

As a further comparison, 22(R)-hydroxycholesterol and 22(S)-hydroxycholesterol ("22S-OH") were tested under the same conditions, and the results are shown in the bar graph of FIG. 14b, using the same bar indications as those in FIG. 14a. No effect on either INV or TG'ase mRNA was observed in the 22S-OH data, while the 22R-OH data repeated what was observed in FIG. 14a.

Figure 15:
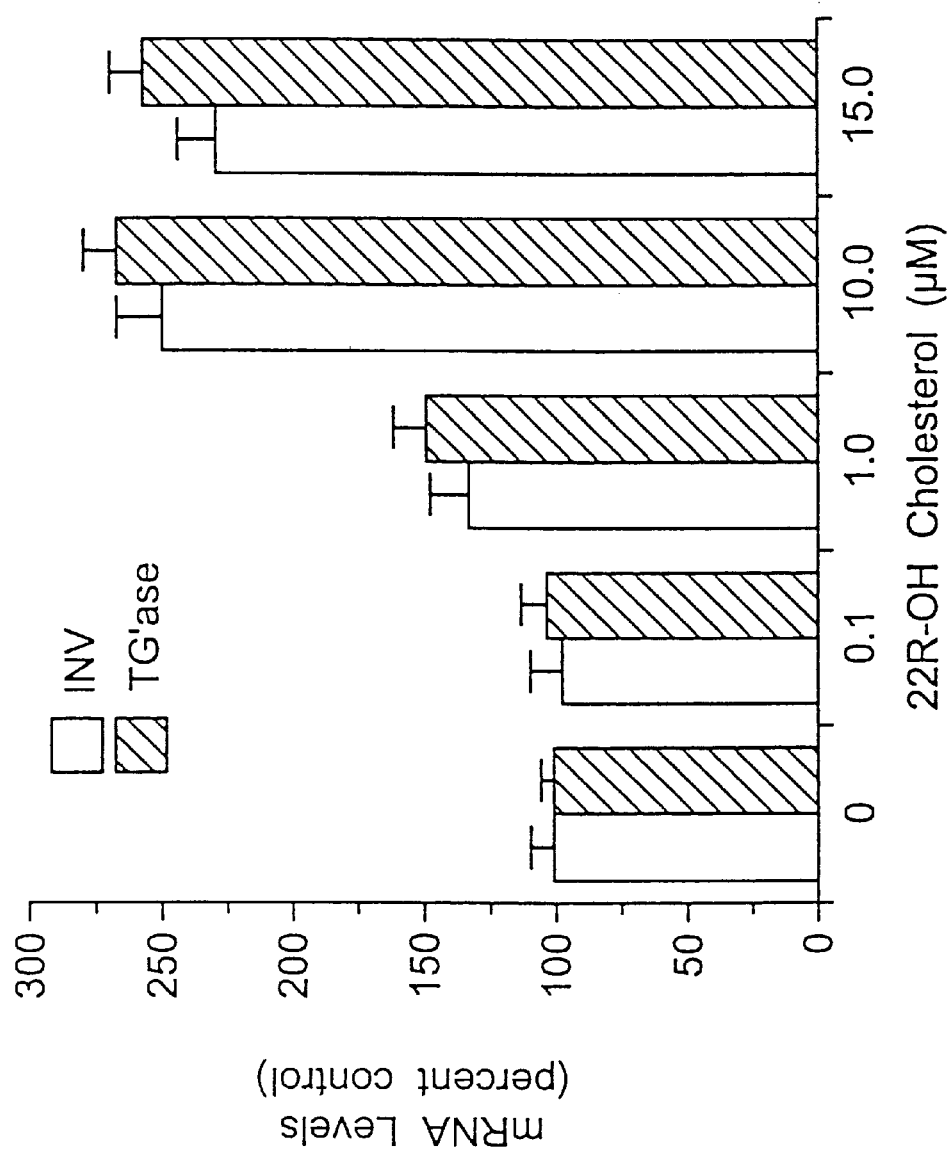
FIG. 15 is a bar graph showing the dependency of involucrin and transglutaminase mRNA levels on the dosage of an LXRα activator.

The dose dependency of 22(R)-hydroxycholesterol was then determined, using doses of 0, 0.1 μM, 1.0 μM, 10.0 μM, and 15.0 μM. The results are shown in the bar graph of FIG. 15, using the same bar indications for INV and TG'ase mRNA as in FIGS. 14a and 14b. The plot indicates that maximal effects were seen with a dosage of 10–15μM, and half-maximal effects with approximately 5 μM.

EXAMPLE 13

An extracellular calcium concentration of 1.2 mM is well known to stimulate differentiation in keratinocytes. This example demonstrates that oxysterol activators of LXRα in the presence of a high calcium concentration stimulate keratinocyte differentiation even further.

Figure 16:
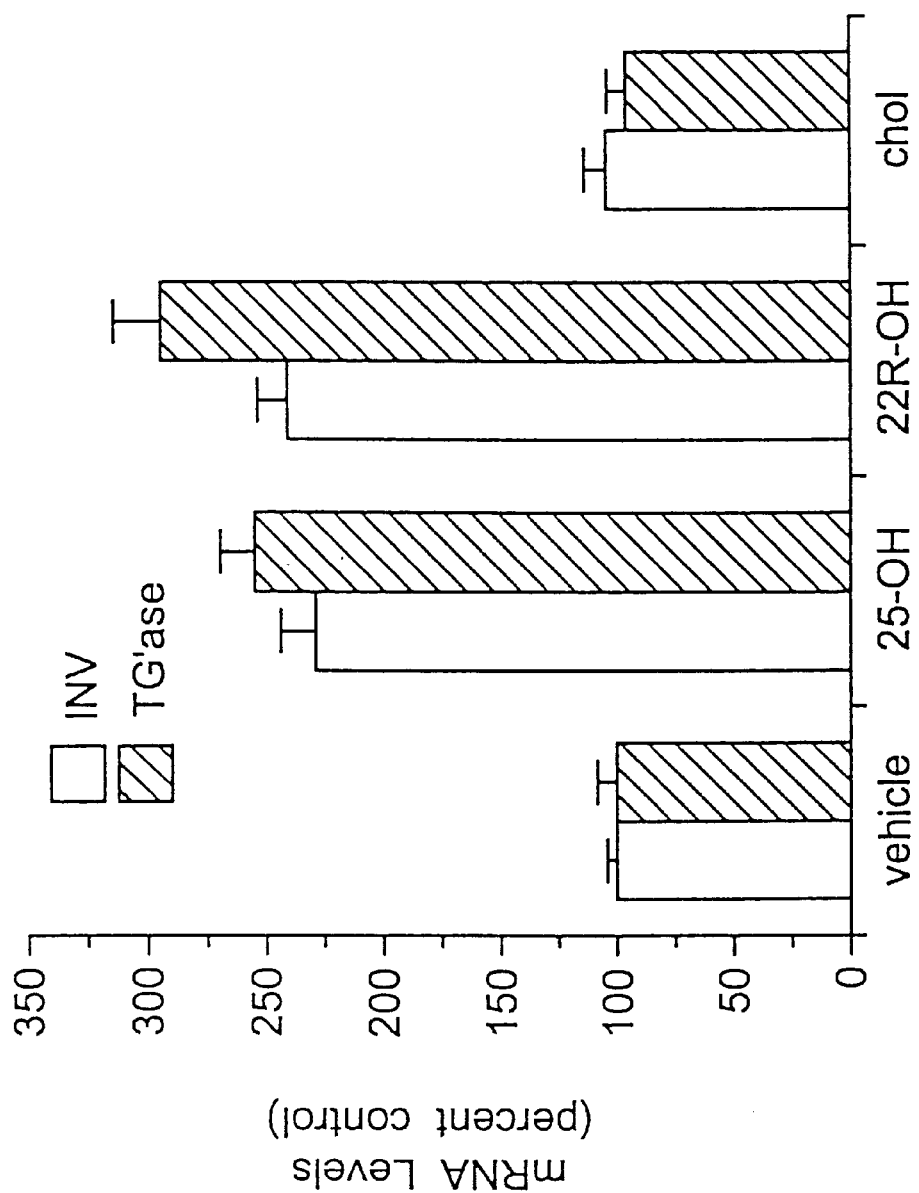
FIG. 16 is a bar graph showing results similar to those of FIGS. 14a and 14b except using a cell culture with a higher calcium content.

The experiment of Example 12 was repeated except that the calcium concentration was raised to 1.2 mM and only the vehicle alone and the vehicle plus 25-hydroxycholesterol (10 μM), 22(R)-hydroxycholesterol (10 μM), or cholesterol (10 μM) were tested. The results are shown in the bar graph of FIG. 16, using the same bar indications as in the preceding figures. The bar graph of FIG. 16 shows that 25-hydroxycholesterol and 22(R)-hydroxycholesterol both induced mRNA levels of both INV and TG'ase, INV by approximately 2.3–2.4 times the control, and TG'ase by approximately 2.5–2.9 times the control, while cholesterol had no effect on either. Determinations were also made of β-actin mRNA levels, and the results (not shown in the Figures) indicated that these levels were unaffected by oxysterol treatment in either low (0.03 mM) or high (1.2 mM) calcium conditions.

EXAMPLE 14

This example demonstrates that the oxysterol activators of LXR stimulate protein levels of involucrin and transglutaminase, while cholesterol does not.

Figure 17A:
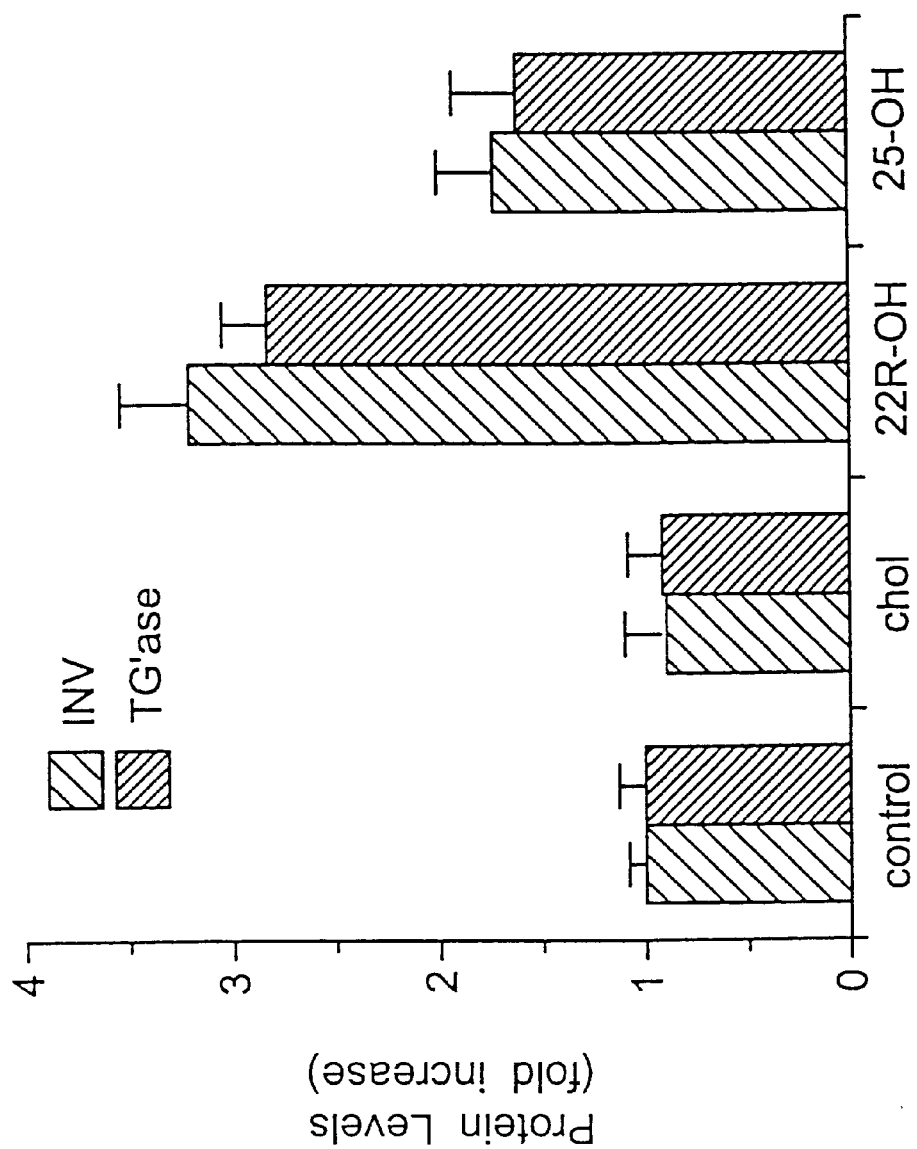
FIG. 17a is a bar graph showing involucrin and transglutaminase protein levels in cell cultures treated with two LXRα activators as well as one treated with cholesterol for comparison.

Levels of involucrin and transglutaminase protein were measured in keratinocytes incubated in low calcium (0.03 mM) and treated with the test compounds for 24 hours. The results are shown in the bar graph of FIG. 17a, where the test compounds are compared with the vehicle alone (control) and cholesterol, using the same bar indications as in FIGS. 14 through 16. The plot shows that 25-hydroxycholesterol induced INV levels approximately 1.7-fold and TG'ase protein levels approximately 1.6-fold relative to the control, and that 22(R)-hydoxycholesterol induced INV levels approximately 3.2-fold and TG'ase protein levels approximately 2.8-fold relative to the control. Cholesterol had no effect.

Figure 17B:
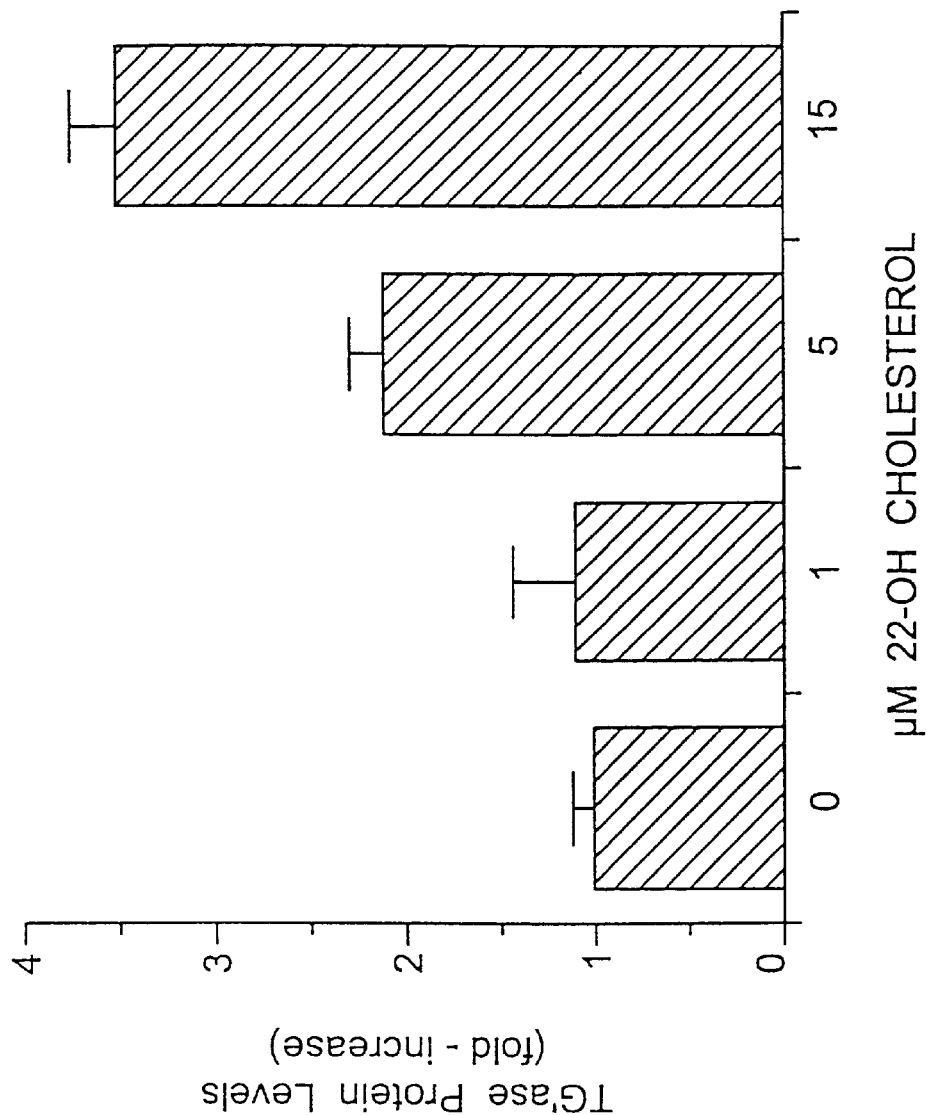
FIG. 17b is a bar graph showing the dependency of the transglutaminase protein level on the dosage of one of the LXRα activators at high calcium concentration.
Figure 17C:
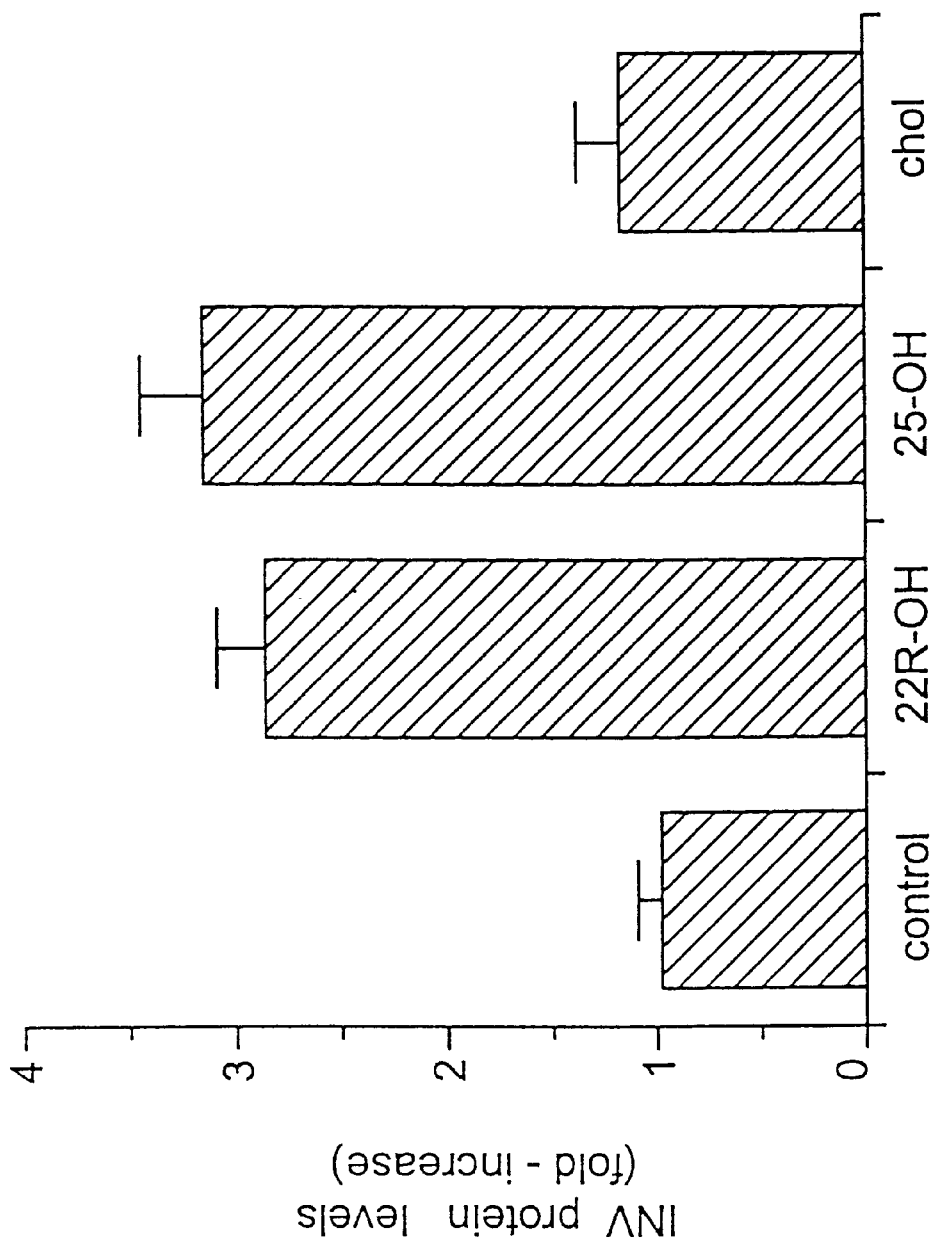
FIG. 17c is a bar graph showing the involucrin protein level in cell cultures treated with two LXRα activators and one with cholesterol at high calcium concentration.

Tests performed in high calcium conditions (1.2 mM) are shown in FIGS. 17b (for 22(R)-hydroxycholesterol only, at three dose levels) and 17c (for 22(R)-hydroxycholesterol, 25-hydroxycholesterol, and cholesterol, all at a dose of 15 $\mu$M). At a concentration as low as 5 $\mu$M, 22(R)-hydroxycholesterol showed a 2.1-fold increase in TG'ase protein level (FIG. 17b). For INV protein, the increase at 15 $\mu$M concentration was 2.8-fold for 22(R)-hydroxycholesterol and 3.2-fold for 25-hydroxycholesterol, with essentially no increase for cholesterol (FIG. 17c).

EXAMPLE 15

Figure 18A:
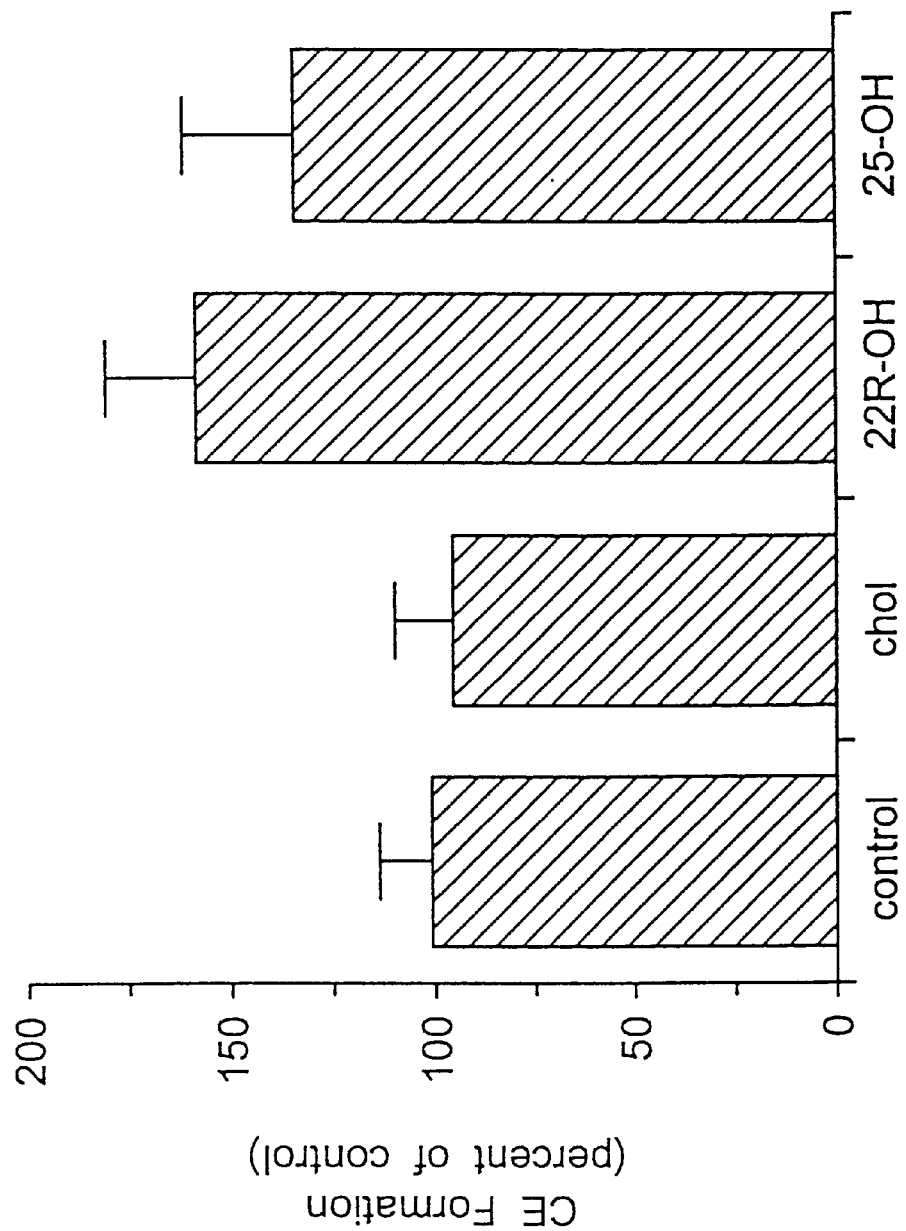
FIG. 18a is a bar graph showing cornified envelope formation in low-calcium cell cultures treated with two LXRα activators as well as one treated with cholesterol for comparison.
Figure 18B:
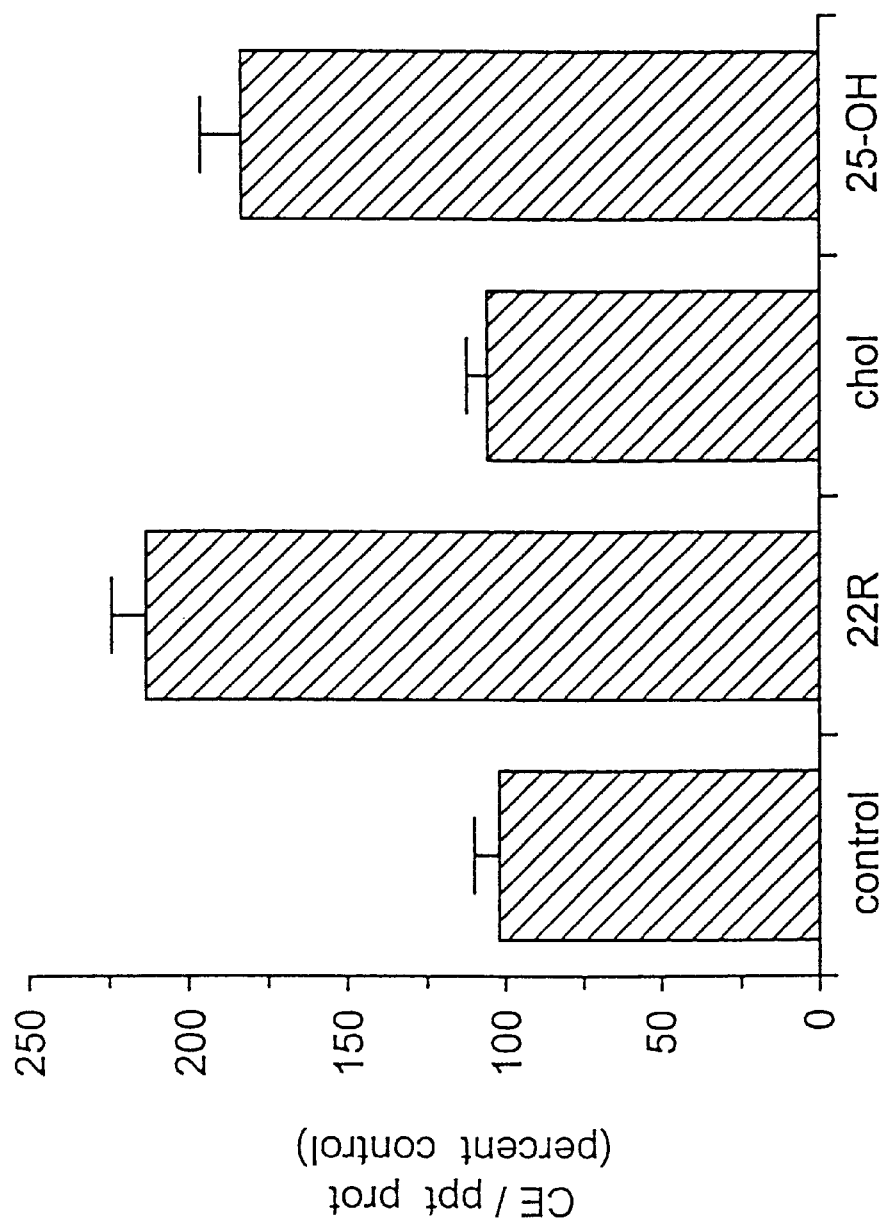
FIG. 18b is a bar graph showing similar results in high-calcium cell cultures.

An additional measure of keratinocyte differentiation is the rate of cornified envelope formation. Using the procedures set forth in the Materials and Methods section above, 25-hydroxycholesterol (10 $\mu$M) and 22(R)-hydroxycholesterol (10 $\mu$M) were compared with cholesterol (10 $\mu$M) and the vehicle alone (control), with treatment for 48 hours under both low calcium (0.03 mM) and high calcium (1.2 mM) conditions. The results are shown in the bar graphs of FIGS. 18a (low calcium) and 18b (high calcium). The low calcium results (FIG. 18a) showed that treatment with 25-hydroxycholesterol yielded a 1.6-fold increase in cornified envelope (CE) formation, and treatment with 22(R)-hydroxycholesterol yielded a 1.3-fold increase. The high calcium results (FIG. 18b) showed that treatment with 25-hydroxycholesterol yielded a 1.75-fold increase in CE formation, and treatment with 22(R)-hydroxycholesterol yielded a 2.1-fold increase. Cholesterol itself produced no increase in either low or high calcium conditions.

EXAMPLE 16

This example demonstrates that oxysterol activators of LXR$\alpha$ inhibit proliferation of keratinocytes, as indicated by the rate of DNA synthesis in keratinocytes. Oxysterols are known to be potent inhibitors of cell growth in other cell types such as thymocytes and lymphocytes.

Figure 19:
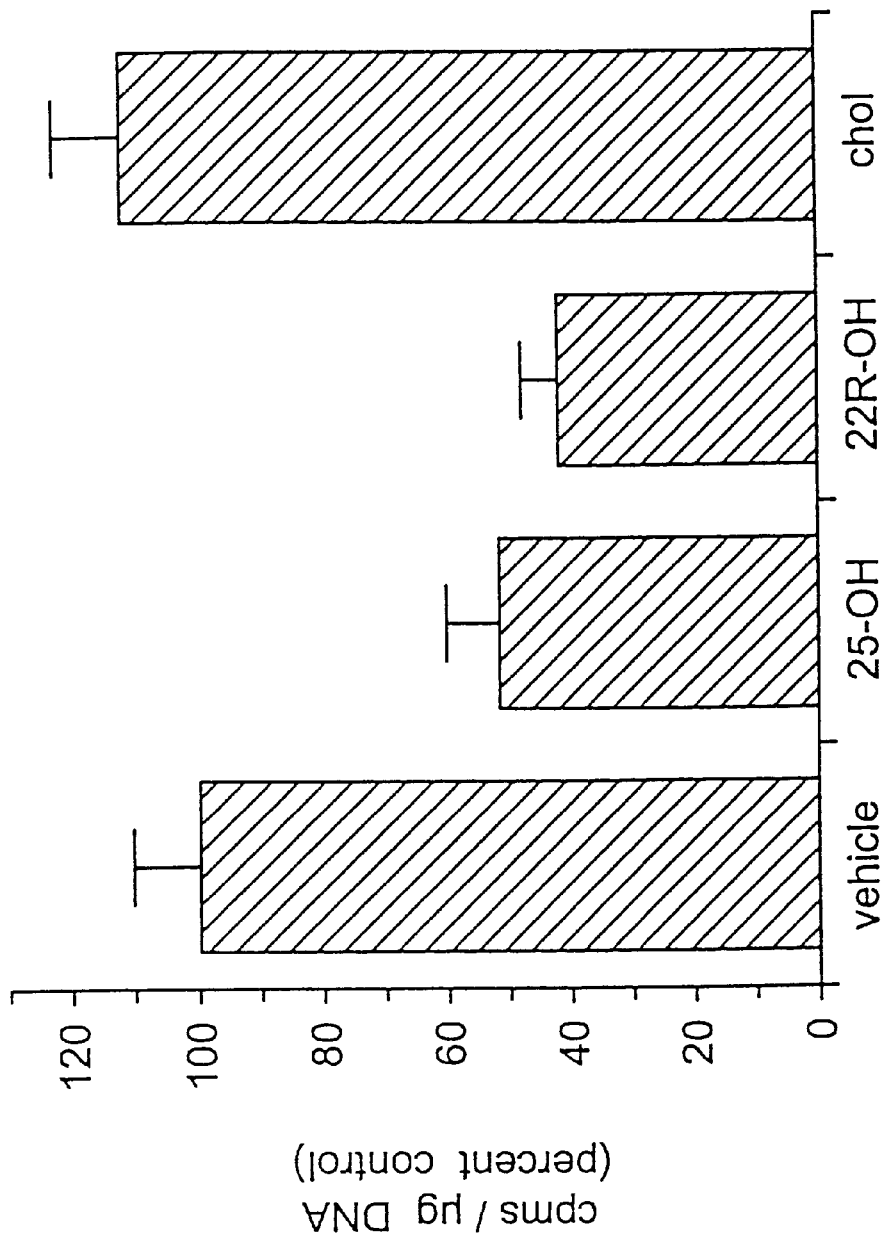
FIG. 19 is a bar graph showing the rate of DNA synthesis in low-calcium cell cultures treated with two LXRα activators as well as one treated with cholesterol for comparison.

Using the procedures set forth in the Materials and Methods section above, 25-hydroxycholesterol (10 $\mu$M) and 22(R)-hydroxycholesterol (10 $\mu$M) were compared with cholesterol (10 $\mu$M) and the vehicle alone (control), with treatment for 24 hours under low calcium (0.03 mM) condition. The results are shown in the bar graph of FIG. 19. The bar graph shows that 25-hydroxycholesterol decreased the rate of DNA synthesis to 50% of the control, and 22(R)-hydroxycholesterol reduced the rate to 42% of control, during the 16-hour time period in which the DNA synthesis was measured. In contrast, cholesterol modestly but significantly increased DNA synthesis (117% of control).

EXAMPLE 17

This example explores whether the increase that oxysterols cause in INV and TG'ase mRNA levels is related to the fact that these oxysterols inhibit the enzyme HMG CoA reductase, which is the rate-limiting enzyme of cholesterol synthesis and which leads to decreased levels of isoprenoids. To anwer this question, tests similar to those described in Example 12 above were performed in the presence and absence of mevalonate, which is the earliest product of HMG CoA reductase.

The tests measured INV and TG'ase mRNA levels in keratinocytes treated with 25-hydroxycholesterol (10 $\mu$M), alone or in the presence of mevalonate (10 $\mu$M), as well as mevalonate alone (10 $\mu$M), for 24 hours. Treatment with mevalonate alone had no effect on the INV and TG'ase mRNA levels. Treatment with 25-hydroxycholesterol, both alone and in the presence of mevalonate, resulted in a two-fold increase in the INV and TG'ase mRNA levels. The conclusion is that inhibition of HMG CoA reductase is not the basis for the increase in INV and TG'ase mRNA levels caused by oxysterols.

The foregoing is offered primarily for purposes of illustration. It will be readily apparent to those skilled in the art that the concentrations, operating conditions, materials, procedural steps and other parameters of protocols described herein may be further modified or substituted in various ways without departing from the spirit and scope of the invention.

We claim:

1. A method for treating the epidermis of a terrestrial mammalian subject suffering from a perturbed epidermal barrier function, said method comprising topically applying to said epidermis a topical composition comprising an activator of peroxisome proliferator-activated receptor $\alpha$ in an amount effective in enhancing barrier development.

2. A method in accordance with claim 1 in which said activator is a member selected from the group consisting of linoleic acid, oleic acid, 5, 8, 11, 14-eicosatetraynoic acid, 4-chloro-6-(2,3-xylidino)-2-pyrimidinyl)thioacetic acid, clofibrate, and gemfibrozil.

3. A method in accordance with claim 1 in which said activator is linoleic acid.

4. A method in accordance with claim 1 in which said activator is clofibrate.

5. A method in accordance with claim 1 in which the concentration of said active ingredient is from about 10 $\mu$M to about 1000 $\mu$M.

6. A method in accordance with claim 1 in which said active ingredient is clofibrate and the concentration of said active ingredient is from about 100 $\mu$M to about 1,000 $\mu$M.

7. A method in accordance with claim 1 in which said active ingredient is oleic acid and the concentration of said active ingredient is from about 100 $\mu$M to about 1000 $\mu$M.

8. A method in accordance with claim 1 in which said active ingredient is linoleic acid and the concentration of said active ingredient is from about 5 $\mu$M to about 50 $\mu$M.

9. A method in accordance with claim 1 in which said activator is gemfibrozil.

10. A method for treating the epidermis or mucous membrane of a terrestrial mammalian subject suffering from disturbed differentiation or excess epidermis of mucous membrane proliferation, said method comprising topically applying to said epidermis or mucous membrane a topical composition comprising an activator of peroxisome proliferator-activated receptor $\alpha$ in an amount effective in reducing said condition.

11. A method in accordance with claim 10 in which said activator is a member selected from the group consisting of linoleic acid, oleic acid, 5, 8, 11, 14-eicosatetraynoic acid, 4-chloro-6-(2,3-xylidino)-2-pyrimidinyl)thioacetic acid, clofibrate, and gemfibrozil.

12. A method in accordance with claim 10 in which said activator is linoleic acid.

13. A method in accordance with claim 10 in which said activator is clofibrate.

14. A method in accordance with claim 10 in which the concentration of said active ingredient is from about 10 $\mu$M to about 1000 $\mu$M.

15. A method in accordance with claim 10 in which said active ingredient is clofibrate and the concentration of said active ingredient is from about 100 $\mu$M to about 1,000 $\mu$M.

16. A method in accordance with claim 10 in which said active ingredient is oleic acid and the concentration of said active ingredient is from about 100 $\mu$M to about 1000 $\mu$M.

17. A method in accordance with claim 10 in which said active ingredient is linoleic acid and the concentration of said active ingredient is from about 5 $\mu$M to about 50 $\mu$M.

18. A method in accordance with claim 10 in which said activator is gemfibrozil.

* * * * *